(12) United States Patent
McGrath et al.

(10) Patent No.: US 9,505,770 B2
(45) Date of Patent: Nov. 29, 2016

(54) ORGANIC PHOTOVOLTAIC DEVICES COMPRISING SOLUTION-PROCESSED SUBSTITUTED METAL-PHTHALOCYANINES AND EXHIBITING NEAR-IR PHOTO-SENSITIVITY

(75) Inventors: Dominic V. McGrath, Tucson, AZ (US); Mayank Mayukh, Tucson, AZ (US); Diogenes Placencia, Bronx, NY (US); Neal R. Armstrong, Tucson, AZ (US)

(73) Assignee: The Arizona Board of Regents of behalf of the University of Arizona, Tuscon, AZ (US)

( * ) Notice: Subject to any disclaimer, the term of this patent is extended or adjusted under 35 U.S.C. 154(b) by 676 days.

(21) Appl. No.: 13/635,324

(22) PCT Filed: Apr. 11, 2011

(86) PCT No.: PCT/US2011/031970
§ 371 (c)(1),
(2), (4) Date: Sep. 14, 2012

(87) PCT Pub. No.: WO2011/127475
PCT Pub. Date: Oct. 13, 2011

(65) Prior Publication Data
US 2013/0008503 A1    Jan. 10, 2013

Related U.S. Application Data

(60) Provisional application No. 61/342,146, filed on Apr. 9, 2010.

(51) Int. Cl.
*H01L 51/46* (2006.01)
*C07D 487/22* (2006.01)
(Continued)

(52) U.S. Cl.
CPC ............ *C07D 487/22* (2013.01); *B82Y 10/00* (2013.01); *H01L 51/0078* (2013.01);
(Continued)

(58) Field of Classification Search
CPC ........... H01L 51/0078; H01L 51/0046; H01L 51/424; H01L 51/4253; H01L 51/4246; H01L 51/46; H01L 51/48; H01L 51/44; H01L 51/448; H01L 51/0053; H01L 31/0256; B82Y 10/00; C07F 5/00; C07F 7/28; C07F 9/00; C07F 5/06; C07D 487/22
USPC ....................................................... 136/263
See application file for complete search history.

(56) References Cited

U.S. PATENT DOCUMENTS

| | | | |
|---|---|---|---|
| 5,380,842 A * | 1/1995 | Itoh ....................... | C07D 209/44 540/128 |
| 2006/0211172 A1* | 9/2006 | Odegard ............... | H01L 21/563 438/108 |

(Continued)

FOREIGN PATENT DOCUMENTS

| | | | |
|---|---|---|---|
| JP | 2009-081424 | * | 4/2009 |
| WO | WO 2008/018936 A2 | | 2/2008 |

(Continued)

OTHER PUBLICATIONS

Dundar et al., Photoconductive Novel Mesomorphic Oxotitanium Phthalocyanine, Journal of Polyhedron, vol./issue 27, pp. 3383-3390 (2008).*

(Continued)

*Primary Examiner* — Jayne Mershon
(74) *Attorney, Agent, or Firm* — Don D. Chai; Hamilton DeSanctis & Cha, LLP

(57) ABSTRACT

Organic photovoltaic (OPV) devices are disclosed. An exemplary device has first and second electrodes and an organic, photovoltaically active zone located between the first and second electrodes. The photovoltaically active zone includes an organic electron-donor material and an organic electron-acceptor material. The electron-donor material includes one or more trivalent- or tetravalent-metal phthalocyanines with alkylchalcogenide ring substituents, and is soluble in at least one organic solvent. This solubility facilitates liquid-processability of the donor material, including formation of thin-films, on an unlimited scale to form planar and bulk heterojunctions in organic OPVs. These donor materials are photovoltaically active in both visible and near-IR wavelengths of light, enabling more of the solar spectrum, for example, to be applied to producing electricity. Also disclosed are methods for producing the metalated phthalocyanines and actual devices.

34 Claims, 19 Drawing Sheets

(51) Int. Cl.
  *B82Y 10/00* (2011.01)
  *H01L 51/00* (2006.01)
  *H01L 51/42* (2006.01)
(52) U.S. Cl.
  CPC ........ *H01L 51/0046* (2013.01); *H01L 51/424* (2013.01); *H01L 51/4246* (2013.01); *H01L 51/4253* (2013.01); *Y02E 10/549* (2013.01); *Y02P 70/521* (2015.11)

(56) References Cited

U.S. PATENT DOCUMENTS

| | | | |
|---|---|---|---|
| 2007/0096085 A1 | 5/2007 | Rand et al. | |
| 2007/0219375 A1* | 9/2007 | Fujiyama | B82Y 10/00 546/278.7 |
| 2008/0035965 A1* | 2/2008 | Hayashi | H01L 27/14647 257/291 |
| 2009/0293946 A1* | 12/2009 | Lin | H01L 51/0003 136/255 |
| 2010/0025665 A1 | 2/2010 | Rand et al. | |
| 2010/0078075 A1* | 4/2010 | Tsukahara | B82Y 10/00 136/263 |
| 2011/0259409 A1* | 10/2011 | Naito | H01L 51/4273 136/255 |
| 2013/0255758 A1* | 10/2013 | Rand | B82Y 10/00 136/255 |

FOREIGN PATENT DOCUMENTS

| | | |
|---|---|---|
| WO | WO 2009/056626 A1 | 5/2009 |
| WO | WO 2009/089470 A2 | 7/2009 |

OTHER PUBLICATIONS

International Search Report and Written Opinion of the International Searching Authority, mailed Sep. 6, 2011, for corresponding International Application No. PCT/US2011/031970, 11 pages.

* cited by examiner

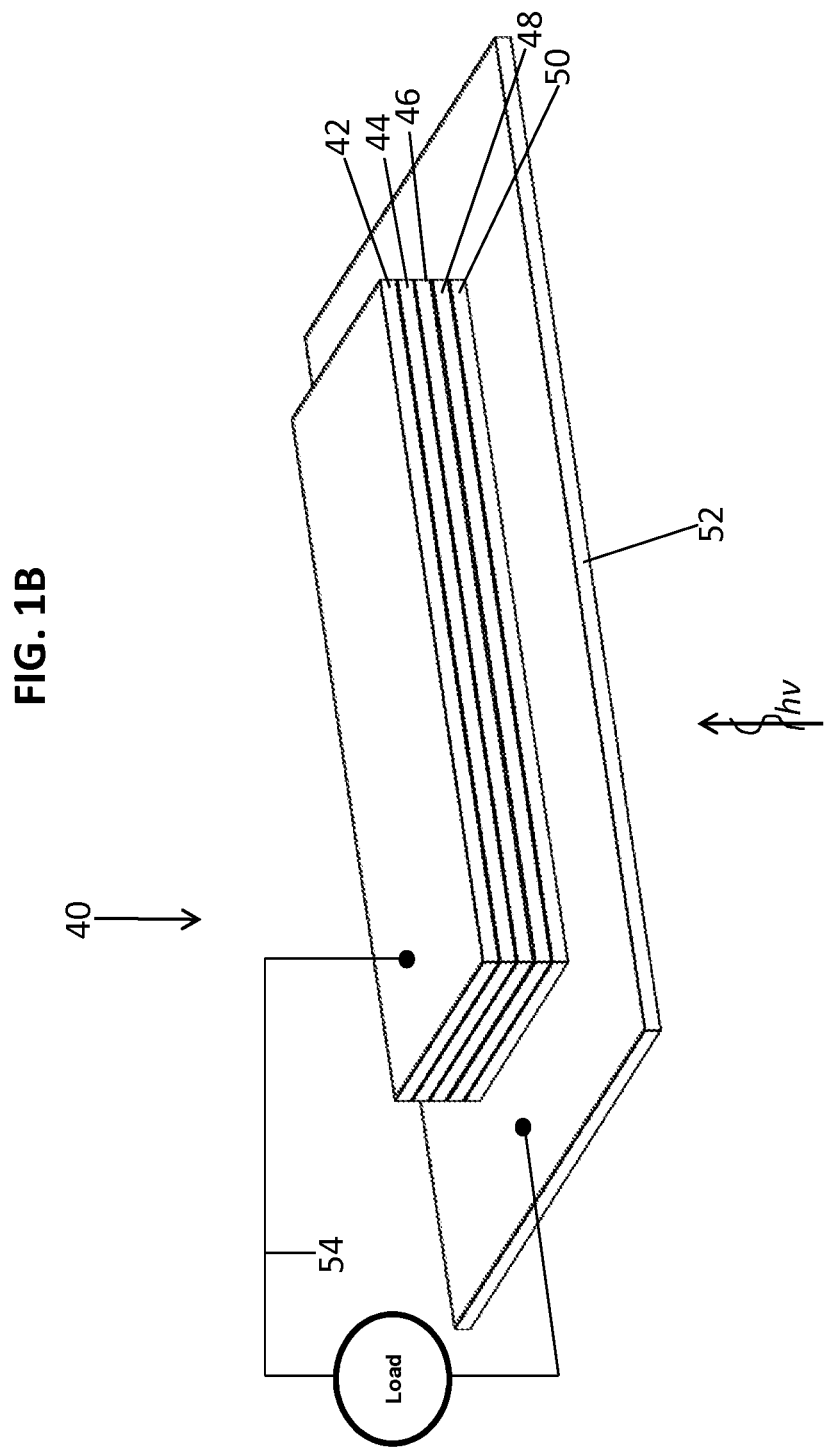

Device#3

Device#4

FIG. 7
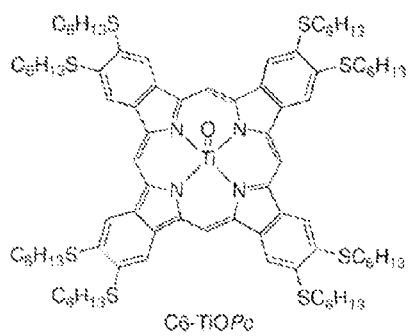
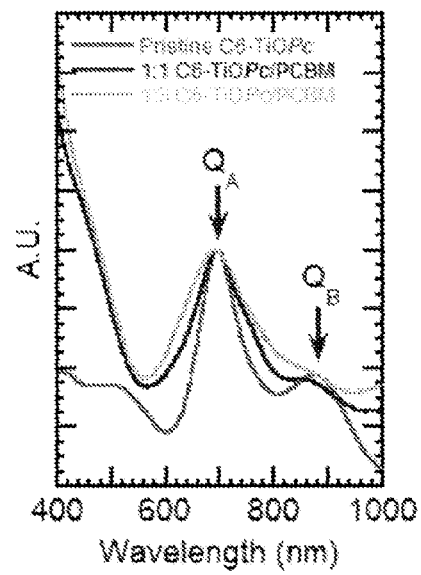
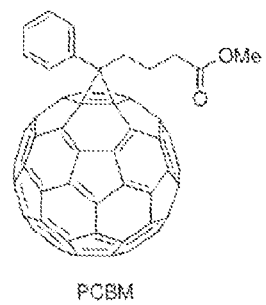
FIG. 8A                FIG. 8B
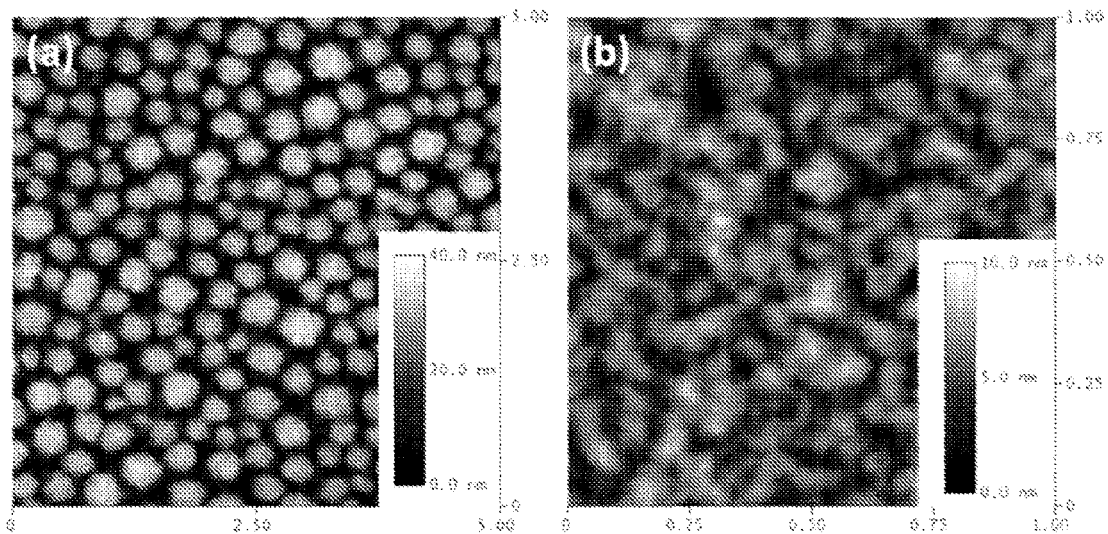

ORGANIC PHOTOVOLTAIC DEVICES COMPRISING SOLUTION-PROCESSED SUBSTITUTED METAL-PHTHALOCYANINES AND EXHIBITING NEAR-IR PHOTO-SENSITIVITY

CROSS-REFERENCE TO RELATED APPLICATIONS

This application is the U.S. National Stage of International Application No. PCT/US2011/031970, filed Apr. 11, 2011, which in turn claims priority to and the benefit of U.S. Provisional Patent Application No. 61/342,146, filed on Apr. 9, 2010, both of which are incorporated herein by reference in their respective entireties.

ACKNOWLEDGMENT OF GOVERNMENT SUPPORT

This invention was made with government support under grant number CHE0719437 awarded by the National Science Foundation and grant number DE-SC0001084 awarded by the U.S. Department of Energy. The U.S. government has certain rights in the invention.

FIELD

This disclosure pertains to, inter alia, organic photovoltaic devices and methods for their manufacture, and to devices comprising same.

BACKGROUND

A substantial amount of world energy production is by combustion of fossil fuels. As global energy demands relentlessly increase, fossil fuels are becoming exhausted and are also implicated in the progressively increasing concentration of carbon dioxide in the earth's atmosphere, which according to the intergovernmental panel on climate change (IPCC) predictions, will reach the critical limit by 2030 if we continue to do business as usual. Hence, a key challenge facing world industrial economies is the development of environmentally benign, renewable energy. A significant technology currently under intense development for producing renewable energy is photovoltaic (PV) cells, which directly convert incident light into electricity. The produced electrical power can be used for driving any of various electrical loads such as, for example, lighting, heating, or operation of electronic equipment. Other uses include charging of batteries or other energy storage devices.

PV cells produce direct-current electricity by the photovoltaic (PV) effect, in which a voltage or electrical current is produced in a photoconductive material by exposing the material to light of one or more particular wavelengths. The PV effect is different from the photoelectric (PE) effect. Whereas the PE effect involves ejection of electrons from a material that is exposed under certain conditions to light, the PV effect involves light-induced shifting of electrons of a photoconductive material from lower to higher energy bands (e.g., from a valence band to a conduction band) when the material is illuminated by light of a certain wavelength(s). As discussed more fully below, this electron shifting produces a potential difference across electrodes in contact with the photoconductive material and can produce sufficient electrical current to drive a load. Substantially all PV devices are like photodiodes, wherein the term "photovoltaic" denotes the unbiased operating mode of a photodiode, wherein current through the photodiode is produced entirely by incident light energy.

Most PV cells currently in use are made of a rigid, inorganic semiconductor material such as crystalline silicon, gallium arsenide, copper indium selenide, or cadmium telluride. Unfortunately, these cells and panels thereof are expensive, particularly as a result of the complexity of processes for purifying and converting raw materials for use in these cells. For example, solar-grade silicon is very high purity, which is expensive to produce. Also, crystalline materials, especially having a large surface area, are difficult to produce due especially to problems associated with producing large crystals that do not have a significant density of efficiency-degrading defects. These materials also raise concerns about their disposal in a responsible manner, especially on a large scale.

More recent approaches to making PV cells stemmed from discoveries of the photovoltaic behavior of certain organic molecules, including certain polymers and small-molecule chromophores, called "conjugated" materials. The molecular structure of a conjugated material includes alternating single and double bonds of adjacent carbon atoms; e.g., a conjugated organic polymer has a carbon backbone comprising alternating single and double covalent bonds of the carbon atoms. Compared to conventional semiconductors such as silicon, conjugated compounds are relatively easy to produce and incorporate into products. Many are mechanically flexible and are relatively easy to dispose of in an environmentally sensible manner. Compared to silicon, these materials have low mass and can be produced at substantially lower cost. Also, many of these compounds are relatively easily processed in a manner useful for making PV devices, such as forming them into films using conventional techniques.

An organic PV cell generally functions by undergoing the following four physical processes: (a) absorption of light, (b) diffusion of the excited state ("exciton") to the heterojunction, (c) light-induced charge-transfer (i.e., separation of opposite charges) and charge transport toward respective electrodes, and (d) charge collection at the electrodes. To such end, a typical organic PV cell comprises a "photoactive layer" that includes a first substance termed an "electron donor" or simply "donor" and a second substance termed an "electron acceptor" or simply "acceptor." The conjugated material is normally the electron donor (also called "electron absorber" or simply "absorber"). The electron donor is the material that absorbs incident photons (having a wavelength absorbable by the material). In the absorber, absorbed photons produce charge pairs (elevated-energy electrons and corresponding "holes") in the material. The acceptor typically has higher electron affinity ("EA") than the donor. Fullerene ($C_{60}$) is often used as an acceptor, especially in planar heterojunction organic PV devices, due to its high electron affinity and its ability to be vapor-deposited.

The donor (D) functions essentially as a p-type semiconductor, and the acceptor (A) functions essentially as an n-type semiconductor. More specifically, the donor functions as an "electron-ejecting" material upon absorption of photon, and the acceptor functions as an "ejected-electron accepting" material. Upon encountering an incident photon (hv) of proper wavelength, the following photo-excitation reaction occurs with the donor and acceptor:

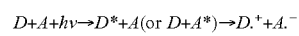

$$D + A + h\nu \rightarrow D^* + A \text{ (or } D + A^*) \rightarrow D^{\cdot +} + A^{\cdot -}$$

in which $D^*$ and $A^*$ are the excited state of the donor and acceptor, respectively. Photo-excitation is followed by formation of this charge-separated state, consisting of the radical cation of the donor ($D.^+$) and the radical anion of the acceptor ($D.^-$).

Conjugated materials useful as electron donors have multiple delocalized π electrons that are normally produced by hybridization of carbon p-orbitals in the material's conjugated molecular structure. When excited by an absorbed photon having a particular wavelength, a π electron is excited to delocalize from a highest occupied molecular orbital (HOMO) to a lowest unoccupied molecular orbital (LUMO). This delocalization jump is called a π-π* transition, in which π denotes the bonding orbital (HOMO) of the electron, and π* denotes a corresponding anti-bonding orbital (LUMO) of the electron. (The hole is regarded as being in the HOMO.) The energy "bandgap" is the separation between the LUMO and HOMO, which is related to the particular absorbed wavelength of light. The electron experiencing the π-π* transition produces a corresponding "hole," and the electron and hole are collectively termed an "electron-hole pair."

An "exciton" in a photo-active material is an electron-hole pair in a bound state. An exciton has a defined lifetime before undergoing geminate recombination, i.e., a process in which the original electron and hole recombine with each other rather than recombining with holes or electrons from other pairs. To produce a photo-current the electron and hole of a given exciton must separate from each other. Otherwise, they may recombine. For the material to produce a useful electrical current, the electron and hole must be collected separately at respective electrodes before they can recombine.

In most organic PV devices ("OPV" devices) the donor and acceptor materials are sufficiently dissimilar that they are at least partially non-miscible with each other. As a result, in an OPV device, respective units of each material contact each other at one or more "heterojunctions" that are effectively p-n interfaces. The (singlet) excitons diffuse through the donor layer toward the heterojunction via Forster energy transfer. At the interface, the electrons become separated from the holes, a process called "exciton dissociation." Exciton dissociation also results in the electron energy dropping from the conduction band of the donor to the conduction band of the acceptor. (These conduction bands have respective edges, and the band edge of the acceptor should be lower than the band edge of the donor to ensure proper charge migration.) From the dissociated exciton and if the charge-carrier mobility of the active material is sufficient, the electron and hole (as respective "charge carriers") are collected at respective electrodes of the OPV device. If the charge-carrier mobility of the active material is too low in view of the mean distance in the material to a p-n interface, the charge carriers do not reach the electrodes, instead undergoing recombination (via intrinsic radiative and non-radiative decay processes), for example, or remaining uncombined and possibly interfering with migration of other charge carriers in the cell.

Conventional OPV devices (also called "OPV cells") have one of two general structural configurations. One configuration is termed a "planar heterojunction," in which a layer of photoactive material (comprising a layer of the donor and a layer of the acceptor) is sandwiched between the electrodes in a planarly laminar configuration. One of the electrodes is transparent to at least certain useful wavelengths of incident light (especially the wavelength(s) that produce excitons in the donor material), and the other electrode usually is reflective to the incident light. The interface between the donor and acceptor layers constitutes the junction, which is called a "heterojunction" because the donor and acceptor are different materials. Desirably, excitons created in the donor layer diffuse to the heterojunction, where the charges separate from each other, with the hole remaining in the donor and the electron passing into the acceptor on its way to a respective electrode.

Planar heterojunctions are easy to form but tend be inefficient. Excitons typically have diffusion lengths of approximately 3 to 10 nm in a photoactive material. This requires that the donor and acceptor layers be very thin to facilitate successful diffusion of charges to the electrodes. Generally, the thinner the photoactive material, the less light it can absorb. The less light that is absorbed, the fewer excitons that are produced, and the lower the efficiency of the cell. Thicker layers do not absorb significantly more light than a thinner film, but they do exhibit a large series resistance.

The second structural configuration is termed a "bulk heterojunction" ("BHJ"), in which the layer of photoactive material is a mixture of the donor and acceptor materials. To form a BHJ, the donor and acceptor materials should be immiscible, and when they are mixed together they tend to phase-separate from each other. Appropriate agitation during mixing can produce a donor-acceptor mixture in which very small bits (in the 1-100 nanometer range) of each material are uniformly distributed throughout the x, y, and z dimensions of the mixture. This mixture forms a corresponding distribution of very small p-n junctions throughout the "bulk" of the photoactive material. Desirably, the bits of donor and acceptor have a mean separation from one another by distances in the range of approximately 5-10 nm (the usual range of diffusion length of the excitons) to increase the probability of successful charge diffusion to the heterojunctions and correspondingly to reduce the probability of carrier recombination. Thus, although BHJs are less limited in terms of active-material thickness, the performance of conventional BHJ cells is affected by many variables that are difficult to control or maintain at a consistent level.

Basically, the overall efficiency of an OPV cell is the ratio of electrical power the device can deliver to a load, relative to the light power incident on the device. Efficiency is expressed in several different ways. The "quantum efficiency" ("QE") of the cell is the ratio of the number of charge carriers (excitons) produced by the cell to the number of photons of a particular wavelength (and thus of a particular energy) incident on the cell. For example, if all the incident photons of a certain wavelength are absorbed and converted into respective excitons, then the QE of the cell for the wavelength would be unity. This is an ideal situation that is not met with current PV technology because of efficiency-robbing phenomena normally occurring in the cell such as: (a) short exciton lifetime and diffusion length, (b) geminate and bimolecular recombinations of excitons before they reach the heterojunctions, (c) lack of precise control over the morphology of the active layer, (d) poor mobility of charge carriers, and (e) reflection and scattering of incident light. QE is of two types: external quantum efficiency (EQE) and internal quantum efficiency (IQE). EQE is a ratio of the number of charge carriers produced and collected by the OPV cell to the number of photons of a given wavelength incident on the cell. IQE is the ratio of the number of charge carriers produced and collected by the PV cell to the number of photons incident on the cell and absorbed by the cell. IQE is always greater than EQE.

A monochromatic version of EQE is called "Incident Photon to Electron-Conversion Efficiency" or "Incident Photon to Current Efficiency" (abbreviated "IPCE"). IPQE is the ratio of photons actually producing electrons that are delivered by the cell to a load, relative to photons of a particular monochromatic wavelength of light incident on the cell. A monochromatic version of IQE is the "Absorbed Photon to Current Efficiency" (abbreviated "APCE"), which is the ratio of photons actually producing electrons delivered by the cell to a load, relative to photons of a particular monochromatic wavelength light actually absorbed by the cell.

Another expression of efficiency is the cell's energy-conversion efficiency ($\eta$), which is the percentage of power converted (from absorbed light to electrical energy) and collected, when the cell is connected to an electrical load. This term may be calculated using the ratio of the maximum power point ($P_m$) to the incident light irradiance (E, in W/m$^2$) under standard test conditions ("STC"), and the surface area of the cell ($A_c$, in m$^2$):

$$\eta = \frac{P_m}{E \times A_c}$$

STC specifies a temperature of 25° C. and an irradiance of 1000 W/m$^2$ with an air mass 1.5 (AM1.5) spectrum, which corresponds to the irradiance and spectrum of sunlight incident on a clear day on a sun-facing 37° tilted surface with the sun at an angle of 41.81° above the horizon.

Thus, the efficiency of organic PV cells is limited by the number of photons that can be absorbed within the thickness of the layer of photoactive material. For most chromophores, absorption is confined to the visible region of the electromagnetic spectrum; meanwhile, approximately 50% of the AM1.5G solar irradiance is in the near-IR region. The best organic photovoltaic OPV devices currently available are based on active materials comprising poly(3-hexylthiophene)/phenyl-C$_{61}$-butyric acid methyl ester (P3HT/PCBM), which is transparent in the near-IR region. As a result, substantially none of the near-IR radiance is captured by the cell and used to produce electricity. If the absorption of thin layers of photoactive material could be extended to the near-IR with no significant loss in $V_{oc}$, a significant improvement in power-conversion efficiency ($\eta$) would be possible. ($V_{oc}$ is "photovoltage at open circuit," which is the voltage output from the PV cell being irradiated but not connected to a load.)

Various soluble trivalent- and tetravalent-metal-substituted phthalocyanines ("MPcs", wherein M=AlCl, GaCl, InCl, or V=O) are known structurally and for various uses such as optical limiting devices and donor layers in organic photovoltaics ("OPVs"). Trivalent and tetravalent metal phthalocyanines exhibit higher photoactivity, ionization potentials, charge-generation efficiency, and non-linear susceptibility compared to divalent-metal phthalocyanines (e.g., CuPc), making the trivalent and tetravalent Pcs better candidates for use in OPV devices. The presence of a dipole in the axial direction in these MPcs, perpendicular to the molecular plane, assists the formation of various polymorphs, some of which being photosensitive in the near-IR portion of the electromagnetic spectrum. Polymorphism is the ability of certain molecules to crystallize into different structural forms (unit cells). For example, thin films of TiOPc have been made that include any of several crystalline polymorphs of the compound. But, this compound has not been made soluble so that thin films could be formed of it using solvent-processing techniques.

Poor solubility of trivalent and tetravalent metal phthalocyanines in common organic solvents necessitates: (a) purification by non-ideal methods such as entrainer sublimation and (b) processing by expensive vapor-deposition. Hence, soluble MPc derivatives are needed that can be purified using column-chromatography and processed into thin-films using techniques such as reel-to-reel wet-coating and ink-jet printing. In this context, successful results from attempts to obtain MPc polymorphs from solution-processed films have been elusive. For example, as reported in the literature, spin-coated films of t-butyl-substituted TiOPc derivatives do not lead to near-IR active polymorphs. The TiOPc derivatives reported hereinbelow lend themselves into polymorphs with tunable near-IR sensitivity when layered (e.g., by spin-coating), as a solution in a common organic solvent, on a selected substrate. However, to the best of Applicants' knowledge, these soluble derivatives have not heretofore been used as electron donors for organic PV devices.

In view of the foregoing, there remains a need for organic PV devices providing greater efficiency (including ability to absorb near-IR light) and that can be fabricated by solution-processing on any of various substrates, including rigid and flexible substrates.

SUMMARY

The shortcomings of conventional devices and methods and the industrial needs summarized above are cured by various aspects of this invention. One aspect is directed to organic photovoltaic devices, of which an embodiment comprises first and second electrodes and an organic, photovoltaically active zone located between the first and second electrodes. The photovoltaically active zone comprises an organic electron-donor material and an organic electron-acceptor material. The electron-donor material comprises one or more trivalent- or tetravalent-metal phthalocyanines with alkylchalcogenide ring substituents and is soluble in at least one organic solvent. The photovoltaically active zone can be configured as a planar heterojunction or as a bulk heterojunction. In the planar heterojunction the donor and acceptor materials are formed as respective layers, and the planar interface between the first and second layers constitutes the planar heterojunction.

By way of example, the electron-donor material forming the planar heterojunction comprises at least one ($C_{5-12}$ alkyl)thio-substituted M-phthalocyanine (M-OPc), wherein M is a trivalent or tetravalent metal (e.g., Ti=E, V=E, X—Al, X—Ga, or X—In, wherein E is O, S, or Se, and X is Cl, Br, or I).

More specifically, the photovoltaically active donor material comprises one or more compounds having the molecular formula:

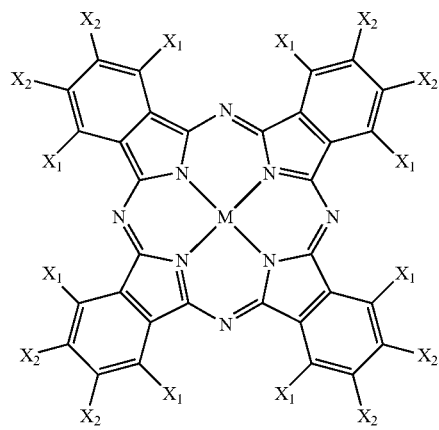

wherein M is a trivalent or tetravalent metal as summarized above; $X_1$ is independently H, OR, or SR; $X_2$ is independently H, OR, or SR; OR is —O—R, where R is an alkyl or other hydrocarbon substituent containing 5-12 carbon atoms; SR is —S—R, where R is an alkyl or other hydrocarbon substituent containing 5-12 carbon atoms; and H is a hydrogen atom.

These substituent groups not only confer solubility of the phthalocyanine chromophore in volatile solvents, which makes device fabrication relatively easy compared to conventional devices, but also enable the devices to be photovoltaically responsive to visible and near-IR wavelengths of incident light. The devices exhibit good photovoltaic efficiency, are easy to manufacture, and are unlimited in terms of physical size. They exhibit good operational parameters such as open-circuit photopotentials ($V_{oc}$). The devices are useful in a wide range of applications, including substantially any application in which conventional photovoltaic devices are currently being used and also in new applications requiring large or otherwise size-unlimited PV devices at reasonable cost. Because the devices produce electrical power not only from visible wavelengths of light but also from near-IR wavelengths, thereby utilizing a greater portion of the electromagnetic spectrum of the sun, for example, than most conventional PV devices, the devices have the tantalizing prospect of producing more power from a given dose of sunlight than conventional PV devices.

Other aspects of the invention pertain to any of various electronic devices represented by a combinations of an OPV device as summarized above, a load, and a circuit connecting the OPV device to the load. Thus, encompassed herein are a wide variety of electronic devices that receive electrical power from an OPV device to operate the electronic device, charge a battery on the electronic device, and/or deliver the power elsewhere for use. Hence, another aspect of the invention pertains to devices that receive power from an organic photovoltaic device as disclosed herein. Such "devices" include, for example, vehicles, buildings, and a wide range of portable and/or stationary things that receive and utilize power. Any of these things can include one or more photovoltaic devices or be connectable to one or more photovoltaic devices within the scope of this disclosure.

Yet another aspect of the invention pertains to methods for fabricating organic photovoltaic devices. An embodiment of such a method comprises solution-forming a photovoltaically active heterojunction of an electron-donor material and an electron-accepting material. The electron-donor material comprises at least one trivalent- or tetravalent-metal phthalocyanine with one or more alkylchalcogenide ring substituent groups, and each substituent group independently has five to twelve carbon atoms. This heterojunction is then disposed between and in electrical contact with first and second electrodes.

The heterojunction can be a planar heterojunction of the electron-donor and electron-accepting materials, wherein forming the planar heterojunction comprises obtaining a liquid solution of the electron-donor material in an organic solvent; forming the solution into an electron-donor layer in electrical contact with the first electrode; applying a layer of the electron-accepting layer to the electron-donor layer, thereby forming a planar heterojunction; and electrically coupling the second electrode to the electron-donor layer.

The heterojunction alternatively can be a bulk heterojunction of the electron-donor and electron-acceptor materials, wherein forming the bulk heterojunction comprises preparing a solution comprising the electron-donor material in a solvent; adding the electron-accepting layer to the solution to form a liquid mixture of the electron-donor and electron-accepting materials in the solvent; forming the liquid mixture into a layer of which a first surface is in electrical contact with the first electrode; and electrically coupling the second electrode to a second surface of the first electrode.

Yet another aspect of the invention pertains to photovoltaic heterojunctions that comprise an electron-donor material and an electron-accepting material. The electron-donor material comprises a trivalent- or tetravalent-metal phthalocyanine with alkylchalcogenide ring substituent groups, each substituent group having five to twelve carbon atoms, as summarized above. The heterojunction can be a planar or bulk heterojunction, and can be sensitive to at least one wavelength of incident light in the visible spectrum and at least one wavelength in the near-IR spectrum.

Yet another aspect of the invention pertains to electron-donor materials that comprise a trivalent- or tetravalent-metal phthalocyanine with alkylchalcogenide ring substituent groups, each substituent group independently having five to twelve carbon atoms. Included with the scope of this aspect are photosensitive and/or photovoltaic devices comprising this electron-donor material. These include any of various detectors and sensors that are sensitive to incident light; some of these detectors and sensors can be configured as transducers that receive incident light and produce an electronic or other response to it.

Yet another aspect of the invention pertains to photovoltaically active materials that comprise a trivalent- or tetravalent-metal phthalocyanine with alkylchalcogenide ring substituent groups, each substituent group independently having five to twelve carbon atoms. Such materials include substantially pure preparations of such material as well as mixtures and other blends of the photovoltaically active material with other substances. Included within the scope of this aspect are photosensitive and/or photovoltaic devices comprising this photovoltaically active material.

Yet another aspect of the invention pertains to a method for synthesizing a soluble trivalent or tetravalent-metal phthalocyanine with alkylchalcogenide ring substituents. An embodiment of the method comprises obtaining alkylchalcogeno-substituted phthalonitriles having alkyls of at least one selected number of carbon atoms. One way in which to obtain these substituted phthalonitriles is by nucleophilic aromatic substitution of dichlorophthalonitrile with alkylchalcogenols having one or more desired carbon-chain lengths. In the method a melt is prepared of the alkychalcogeno-substituted phthalonitriles in the absence of a solvent therefor. The melted alkylchalcogeno-substituted phalonitriles are heated in the presence of urea and a compound supplying a desired trivalent or tetravalent metal. Thus, the substituted phthalonitriles become macrocylized into a corresponding metalated alkylchalcogeno-phthalocyanine in which the trivalent or tetravalent metal is chelated. An advantage of this synthesis method is that it avoids the formation of undesired byproducts such as $H_2Pc$ byproducts that otherwise make purification of the desired product difficult. The alkylchalcogenyl (—O—R or —S—R, where R is alkyl) side chains can enhance processability of the desired product. The alkylchalcogenyl side chains also provide a convenient way in which to "tune" (e.g., by judicious selection of the side-chain structure, number of carbon atoms, and use of an oxy or thio coupling group) the optical and photovoltaic properties of the product when used in thin-films, such as photovoltaically active thin-films. Thin-films of many alkylchalcogenyl-TiOPc products disclosed here exhibit near-IR absorption substantially the same as vacuum-deposited non-substituted Phase-II TiOPc. Certain products also exhibit an additional red-shifted Q-band due to the presence of thioether groups, for example, at the β-positions. The synthesis method also provides a simple route to various polymorphs whose optical properties are reminiscent of Phase-I and Phase-II crystalline polymorphs. This route is made possible through judicious selection of substituent chain lengths and processing reagents.

The foregoing and additional features and advantages of the subject methods will be more readily apparent from the following detailed description, which proceeds with reference to the accompanying drawings.

BRIEF DESCRIPTION OF THE DRAWINGS

FIG. 1B is a schematic diagram of an organic photovoltaic (OPV) device comprising a bulk heterojunction, according to the second representative embodiment.

FIG. 7 depicts molecular structures of C6-TiOPc (as exemplary donor) and PCBM (as exemplary acceptor) used in bulk heterojunctions described in the second representative embodiment. The plot to the right includes respective absorbance spectra for pristine C6-TiOPc film (red) and C6-TiOPc/PCMB thin-films cast from CHCl$_3$ onto PEDOT:PSS-coated ITO substrates, with C6-TiOPc/PCMB ratios of 1:1 (blue) and 1:3 (green).

FIGS. 8A-8B are respective AFM height images for active-layer thin-films having C6-TiOPc:PCBM ratios of 1:1 (FIG. 8A) and 1:3 (FIG. 8B).

FIG. 16A is an image of the film formed from a 1:1 ratio and concentration of 6 mg/mL. FIG. 16B is an image of the film formed from a 1:1 ratio and concentration of 12 mg/mL. FIG. 16C is an image of the film formed from a 1:1 ratio and concentration of 18 mg/mL. FIG. 16D is an image of the film formed from a 1:3 ratio and concentration of 12 mg/mL. FIG. 16E is an image of the film formed from a 1:3 ratio and concentration of 18 mg/mL. FIG. 16F is an image of the film formed from a 1:3 ratio and concentration of 18 mg/mL, after annealing at 150° C. for 10 min.

DETAILED DESCRIPTION

Figure 1A:
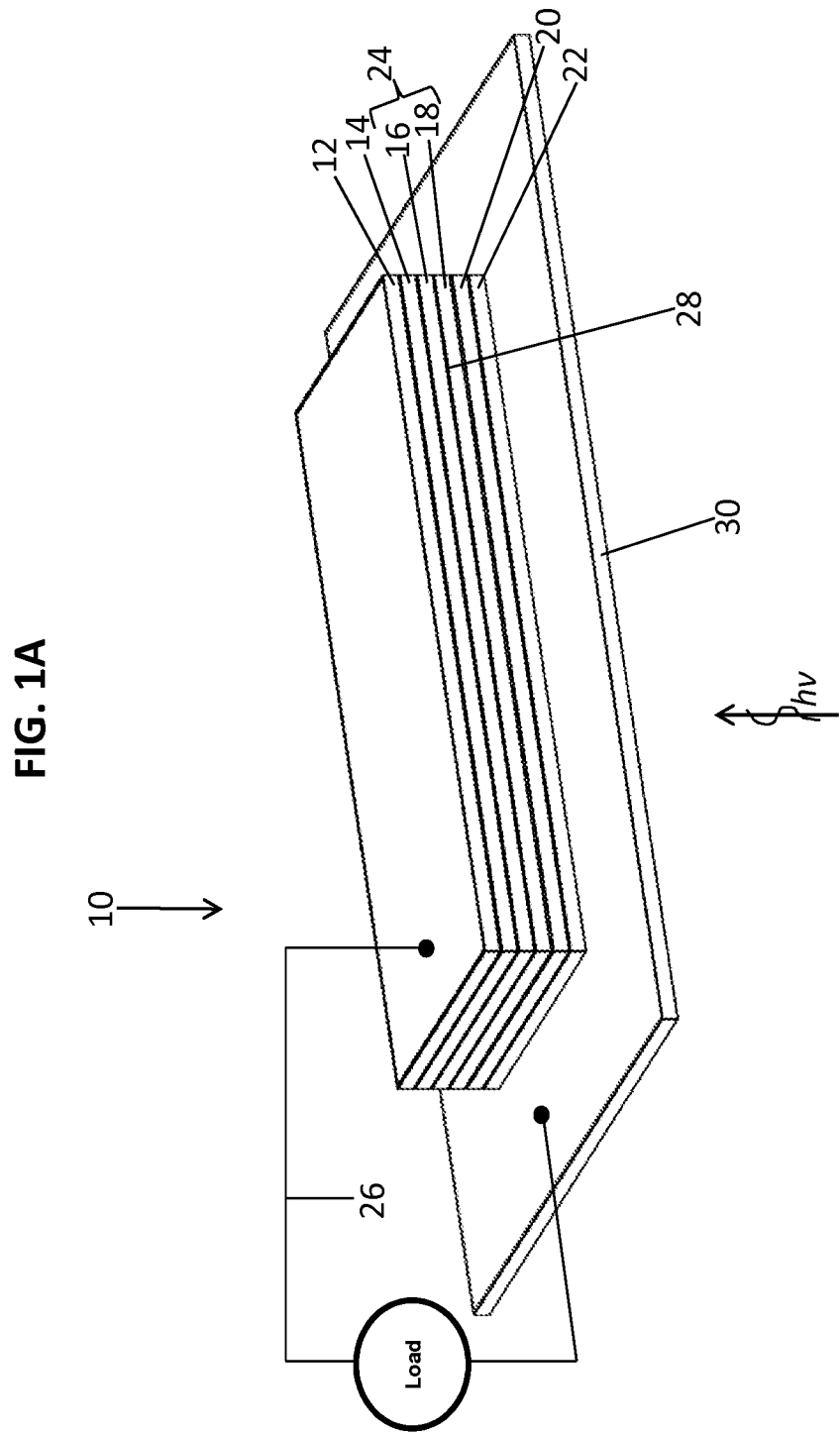
FIG. 1A is a schematic diagram of an organic photovoltaic (OPV) device comprising a planar heterojunction, according to the first representative embodiment.

The invention is described below in the context of representative embodiments that are not intended to be limiting in any way.

As used in this application and in the claims, the singular forms "a," "an," and "the" include the plural forms unless the context clearly dictates otherwise. Additionally, the term "includes" means "comprises." Further, the term "coupled"

encompasses mechanical as well as other practical ways of coupling or linking items together, and does not exclude the presence of intermediate elements between the coupled items.

The described things and methods described herein should not be construed as being limiting in any way. Instead, this disclosure is directed toward all novel and non-obvious features and aspects of the various disclosed embodiments, alone and in various combinations and sub-combinations with one another. The disclosed things and methods are not limited to any specific aspect or feature or combinations thereof, nor do the disclosed things and methods require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed things and methods can be used in conjunction with other things and method. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In the following description, certain terms may be used such as "up," "down,", "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

The terms used in this disclosure generally have their respective ordinary meanings in the art, within the context of the invention and within the specific contexts in which the respective terms are used. Specific terms used herein to describe the invention are discussed as appropriate. Certain terms may be emphasized by enclosing them in quotation marks, for example, but this is not intended to affect the scope and meaning of the term. Similar items or terms may be described or summarized herein in more than one way, including use of synonyms, but no special significance is to be placed upon such descriptions or summaries unless otherwise stated. This disclosure includes descriptions of examples that are intended to be illustrative only and not intended to limit the scope and meaning of the invention or of any exemplified term.

As used herein, the words "about" or "approximately" shall generally mean within 20%, preferably within 10%, and more preferably within 5% of a stated value or range. Numerical quantities given herein are approximate, within the bounds of significant figures, unless stated otherwise.

The organic PV devices disclosed hereinbelow provide the following advantages: (a) They absorb light (or more light) in the near-IR than many conventional devices while also absorbing at least certain wavelengths of visible light, and (b) utilize more of the spectral output of the sun for generation of electrical power. Active materials in these devices comprise electron-donor chromophores that are easy to synthesize and form into heterojunctions of planar and bulk type for use in organic PV devices.

Chromophore Electron Donor Materials

The general class of chromophoric electron-donor materials useful in the subject organic PV (OPV) devices comprises trivalent- and tetravalent-metal phthalocyanines having alkylchalcogenide ring substituents. The alkylchalcogenides each include an alkyl group and a chalcogenide (oxide, sulfide, selenide, or telluride). Each alkyl group desirably has 5 to 12 carbon atoms, more preferably 6 to 10 carbon atoms, and can be branched or straight-chain. The trivalent metals are those normally having a $3^+$ charged ionic state, and tetravalent metals are those normally having a $4^+$ charged ionic state. Phthalocyanine is a highly colored macrocyclic compound that forms coordination complexes with many elements. These complexes, as well as phthalocyanine, are all highly colored and are useful as dyes. Phthalocyanine is strongly absorbent in longer visible wavelengths of light but is highly insoluble in almost every solvent.

The phthalocyanine-based chromophoric electron-donor materials useful as described herein are soluble in at least some common solvents sufficiently to form solutions from which photovoltaically active layers or zones can be cast or otherwise made. The range of compounds called "trivalent or tetravalent-metal phthalocyanines with alkylchalcogenide ring substituents" is encompassed by Table 1, which refers to the following structural formula:

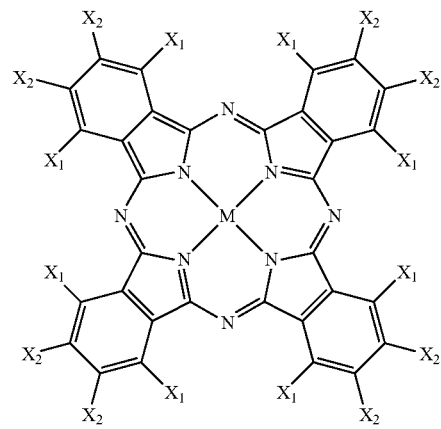

in which:

M is a trivalent or tetravalent metal or metal group as listed;

$X_1$ is independently H, OR, or SR, as listed;

$X_2$ is independently H, OR, or SR, as listed;

OR is —O—R, where R is an alkyl or other hydrocarbon substituent containing 5-12 carbon atoms;

SR is —S—R, where R is an alkyl or other hydrocarbon substituent containing 5-12 carbon atoms;

H is a hydrogen atom; and

C5-C12 are alkyl or other hydrocarbon substituents independently containing 5-12 carbon atoms, respectively.

The "chalcogenide" term in the compound's name reflects the —O— or —S— couplings of the R groups to the phthalocyanine. The $X_1$ and $X_2$ sites are termed "ring sites" (and substituents attached thereto are termed "ring substituents") because these sites are located on respective outer loci on respective rings of the phthalocyanine. In general, the $X_1$ and $X_2$ sites are where the "alkylchalcogenide ring substituents" are located. In a given molecule, not all the $X_1$ and/or $X_2$ sites need be occupied by a respective alkylchalcogenide group (although they all can be). Also, on a given molecule, not all the R groups need have the same chalcogenide coupler (—O— or —S—), although they can all be the same. Hence, the subject compounds also include any compound of which the molecule includes both OR and SR groups in the $X_1$ and/or $X_2$ positions. Also, the R groups on a given molecule need not all be the same. Therefore, the substituents at the $X_1$ and $X_2$ sites are described as being "independent." It also will be understood that the subject compounds also include any mixtures of the specific compounds listed. An exemplary range of compounds is listed in Table 1, in which E is O, S, or Se, and X is Cl, Br, or I.

TABLE 1

| Class | X1 | X2 | R | M |
|---|---|---|---|---|
| 1 | H | OR | C5 | Ti = E, V = E, X—Al, X—Ga, X—In |
| 2 | H | OR | C6 | " |
| 3 | H | OR | C7 | " |
| 4 | H | OR | C8 | " |
| 5 | H | OR | C9 | " |
| 6 | H | OR | C10 | " |
| 7 | H | OR | C11 | " |
| 8 | H | OR | C12 | " |
| 9 | H | SR | C5 | " |
| 10 | H | SR | C6 | " |
| 11 | H | SR | C7 | " |
| 12 | H | SR | C8 | " |
| 13 | H | SR | C9 | " |
| 14 | H | SR | C10 | " |
| 15 | H | SR | C11 | " |
| 16 | H | SR | C12 | " |
| 17 | OR | H | C5 | " |
| 18 | OR | H | C6 | " |
| 19 | OR | H | C7 | " |
| 20 | OR | H | C8 | " |
| 21 | OR | H | C9 | " |
| 22 | OR | H | C10 | " |
| 23 | OR | H | C11 | " |
| 24 | OR | H | C12 | " |
| 25 | SR | H | C5 | " |
| 26 | SR | H | C6 | " |
| 27 | SR | H | C7 | " |
| 28 | SR | H | C8 | " |
| 29 | SR | H | C9 | " |
| 30 | SR | H | C10 | " |
| 31 | SR | H | C11 | " |
| 32 | SR | H | C12 | " |
| 33 | OR | OR | C5 | " |
| 34 | OR | OR | C6 | " |
| 35 | OR | OR | C7 | " |
| 36 | OR | OR | C8 | " |
| 37 | OR | OR | C9 | " |
| 38 | OR | OR | C10 | " |
| 39 | OR | OR | C11 | " |
| 40 | OR | OR | C12 | " |
| 41 | SR | SR | C5 | " |
| 42 | SR | SR | C6 | " |
| 43 | SR | SR | C7 | " |
| 44 | SR | SR | C8 | " |
| 45 | SR | SR | C9 | " |
| 46 | SR | SR | C10 | " |
| 47 | SR | SR | C11 | " |
| 48 | SR | SR | C12 | " |
| 49 | OR | SR | C5 | " |
| 50 | OR | SR | C6 | " |
| 51 | OR | SR | C7 | " |
| 52 | OR | SR | C8 | " |
| 53 | OR | SR | C9 | " |
| 54 | OR | SR | C10 | " |
| 55 | OR | SR | C11 | " |
| 56 | OR | SR | C12 | " |
| 57 | SR | OR | C5 | " |
| 58 | SR | OR | C6 | " |
| 59 | SR | OR | C7 | " |
| 60 | SR | OR | C8 | " |
| 61 | SR | OR | C9 | " |
| 62 | SR | OR | C10 | " |
| 63 | SR | OR | C11 | " |
| 64 | SR | OR | C12 | " |

In Table 1, M also could be ROAl, ROGa, or ROIn. Table 1 is based in part on certain of the listed compounds having been synthesized by Applicants and from reasonable and technically sound extrapolations from observed properties of the synthesized compounds. For example, Applicants have synthesized compounds in which R has six to ten carbons linked by —S— and —O— to the phthalocyanine and in which M is TiO, VO, DAL Can, and CIGa.

The listed range of 5 to 12 carbon atoms for the R groups reflects competing factors of having sufficient R-group carbon length to achieve satisfactory solubility of the substituted phthalocyanine in organic solvent, without having so much R-group length that the metalated phthalocyanines are essentially "diluted" in the photovoltaically active layer. Substituted phthalocyanines in which the R groups are too cumbersome may also not be able to form polymorphs important for near-IR absorptivity and sensitivity, for example. This is discussed more in the first representative embodiment.

First Representative Embodiment

This embodiment is directed to organic photovoltaic (OPV) devices comprising planar heterojunctions ("PHJs") in which a soluble thioalkyl-substituted titanyl phthalocyanine (TiOPc) derivative is used as the electron donor. Thioalkyl-substituted TiOPcs constitute a subgroup of the set of electron donor compounds termed "trivalent- and tetravalent-metal phthalocyanines having alkylchalcogenide ring substituents."

These devices exhibit photo-sensitivity to selected incident wavelengths in the visible region and selected wavelengths in the up to 1 μm (in the near-IR region) wavelength region of the solar spectrum. The devices exhibit good photovoltaic efficiency, are easy to manufacture, and are unlimited in terms of physical size. They exhibit good operational parameters such as open-circuit photopotentials ($V_{oc}$). The devices are useful in a wide range of applications, including substantially any application in which conventional photovoltaic devices are currently being used and also in new applications requiring large or otherwise size-unlimited PV devices at reasonable cost. Because the devices produce electrical power not only from visible wavelengths of light but also from near infrared (near-IR) wavelengths, the devices have the tantalizing prospect of producing more power from a given dose of sunlight than conventional PV devices. To such ends, the devices comprise a photo-active zone comprising at least one election-donor material and at least one electron-acceptor material. The electron-donor material in this embodiment includes a TiOPc chromophore bearing multiple substituent groups. In this embodiment, each substituent group has 6 to 10 carbon atoms, linear or branched. Each substituent group is bonded to the TiOPc chromophore by a —S— (thio) or —O— (oxy) coupling group. These substituent groups not only confer solubility of the chromophore in volatile solvents, which makes device fabrication relatively easy compared to conventional devices, but also enable the devices to be photovoltaically responsive to visible and near-IR wavelengths of incident light. Thus, for producing electricity from light, the devices utilize a greater portion of the electromagnetic spectrum of the sun, for example, than most conventional PV devices.

A schematic diagram of this embodiment 10 is shown in FIG. 1A. The device 10 comprises a first electrode 12, an exciton-blocking layer 14, a layer 16 of an electron-acceptor material, a layer 18 of the electron donor (alkylthio-substituted TiOPc in this embodiment; see FIG. 3), an optional layer 20 of PEDOT:PSS, and a second (transparent) electrode 22. Desirably, the transparent electrode 22 is mounted or otherwise coupled to a suitable substrate 30, which can be rigid or flexible, and that is transparent to at least the wavelengths of incident light to which the donor layer 18 is photovoltaically sensitive. The donor layer 18 and acceptor layer 16 collectively constitute the "photovoltaically-active layer" or "photo-active zone" 24 of the device 10. The electrodes 12, 22 are connected to an external circuit 26 that delivers electrical power produced by the device to a load. The boundary 28 between the donor layer 18 and acceptor layer 16 is a dissociating interface (planar heterojunction) at which electrons of excitons produced photovoltaically in the donor layer 18 are separated from their respective holes.

The electrodes 12, 22 desirably satisfy several criteria. For example, the electrodes 12,22 desirably allow a maximal amount of ambient light to be admitted into the active layer for absorption. Hence, at least one of the electrodes, namely the second electrode 22 in this embodiment, is substantially transparent to the wavelengths to be absorbed by the device 10, thereby allowing such wavelength(s) of incident light (hv) to pass through the second electrode to the photo-active layer 24. The first electrode 12 desirably is reflective to the useful wavelengths of light so that light unabsorbed by a first pass through the photoactive layer 24 may be used in a second pass made possible by reflection of the light from the first electrode. The first electrode 12 functions as an anode in the device 10, since oxidation tends to occur there. The second electrode 22 functions as a cathode since reduction tends to occur there. The electrodes 12, 22 provide respective electrical interfaces between the active layer 24 and conductors external to the device that transfer the charge carriers to or from an external circuit 26. An electrode that is "substantially transparent" to a particular useful wavelength(s) is one that transmits more than 50% of the useful wavelength(s) incident on the electrode. The second electrode 22 is usually made of metal or metal-like material. Candidate metals can be elementally pure metals (e.g., aluminum) or metal alloys. Candidate metal-like materials include, but are not limited to, doped wide-bandgap semiconductors such as indium tin oxide (ITO), gallium indium tin oxide, and zinc indium tin oxide.

The exciton-blocking layer ("EBL") 14 tends to confine the excitons formed in the device 10 to the heterojunction (dissociating interface) 28, thereby limiting the volume through which excitons must diffuse. To such end, the EBL 14 desirably has a LUMO-HOMO bandgap that is greater than the bandgap of the active layer 24. The EBL 14 also desirably is selected so that the electrostatic sign of the carrier (e⁻) is not impeded in passing through the layer. By way of example, the EBL 14 in this embodiment is bathocuprene ("BCP"; see FIG. 3).

For the donor 18 in this embodiment, at least one alkylthio-substituted TiOPc is used. Synthesis of exemplary alkylthio-substituted TiOPc compounds is described later below in the third representative embodiment. TiOPc is a metalated phthalocyanine chromophore comprising a Ti=O bond orthogonal to the molecular plane of the phthalocyanine. The Ti=O moiety is at least partially responsible for shifting absorptivity of this chromophore into the near-IR. Ti=O forms a dipole in the axial direction, which leads to face-to-face arrangements of the metalated phthalocyanine molecules in the donor layer that maximize overlap of their π-orbitals. Depending on the degree of π-orbital overlap in the condensed phase, TiOPc and its alkyl-substituted forms can exist in polymorphs such as Phase-I (or β-phase) and Phase-II (or α-phase) that are active in the near-IR, even in thin-films. This material is characterized by high photoconductivity, third-order non-linear susceptibility, and near-IR absorptivity, all of which being useful attributes for efficient OPV devices and the like.

In contrast to conventional organic photovoltaic devices in which the donor is a polymer, e.g., those based on poly(3-hexylthiophene)/phenyl-$C_{61}$-butyric acid methyl ester (P3HT/PCBM), devices according to this embodiment in which the donor is an alkylthio-substituted TiOPc, is an example of using a relatively small chromophore molecule as the donor. Small molecules are an attractive alternative to polymeric donor materials because they are intrinsically monodisperse and are easy to synthesize and purify.

The substituted metalated phthalocyanines are also amenable to "solution-processing" in which they can be dissolved in a suitable solvent and formed into a photovoltaically active zone by conventional liquid-application techniques. This ability of the material of the donor layer 18 to be dissolved and formed readily into layers while also being photovoltaically sensitive to near-IR wavelengths of light is a key discovery facilitating the advent of devices according to this and other embodiments of the invention. Conventional OPV materials must rely upon conventional techniques such as vacuum-deposition for forming layers thereof, which are expensive and impractical especially for making large OPV devices. I.e., conventional techniques such as vacuum deposition are not scalable. Solution-processing, in contrast, facilitates forming thin films over large areas using techniques such as reel-to-reel wet-coating, spray-coating, screen-printing, doctor-blading, ink-jet printing, spin-coating, or essentially any other liquid-coating process, which can facilitate the formation of large-area, light-weight, low-cost, and flexible devices.

Example alkylthio-substituted TiOPcs are any of the $C_5$, $C_6$, $C_7$, $C_8$, $C_9$, $C_{10}$, $C_{11}$, and $C_{12}$ alkyl-substituted titanyl phthalocyanines. (By way of example, the $C_6$, or hexyl, derivative is denoted C6-TiOPc; see FIG. 3). The alkyl groups can be straight-chain or branched. This range of $C_5$ to $C_{12}$ is not intended to be limiting, but rather represents a generally useful range. Fewer than five or six carbons may not confer sufficient solubility to the substituted TiOPc in the desired organic solvent, and more than twelve carbons may interfere with the substituted TiOPc from forming polymorphs conferring photovoltaic sensitivity to near-IR light. The $C_6$, $C_9$, and $C_{10}$ moieties are especially advantageous based on Applicants' studies to date, in that the compounds do not appear to interfere significantly with formation of desirable polymorphs. More than ten carbons may unacceptably increase the probability of the chromophores forming hexagonal lattices (liquid-crystal-like forms having limited utility as photovoltaic donor materials because of less absorbance in the near-IR region of the electromagnetic spectrum). Since the alkylated substituents are mainly used to render the TiOPc compounds soluble, more than ten to twelve carbons in the substituent groups may "dilute" the chromophore too much in the photovoltaically active layer and thus may reduce the efficiency of the device.

TiOPc provides eight X2 sites (see FIGS. 3 and 7) at which substituent R groups can be attached. These sites are equally reactive, and synthesis of a particular alkyl-substituted TiOPc typically will result in a substituent group attaching at each site. However, it will be understood that alkyl-substituted TiOPCs as used herein encompass TiOPc molecules in which respective alkyl groups are attached to fewer than all eight sites.

Also, the thio (—S—) linkage of the alkyl groups to the TiOPc molecule reflects the particular synthetic route by which the alkyl groups were attached to it. For example, the third representative embodiment pertains to, inter alia, a synthetic scheme involving the favorable reaction of alkylthio-substituted phthalonitriles with $Ti(iOPr)_4$. Hence, it will be understood that alkyl-substituted TiOPcs can have couplings other than thio (—S—) couplings, such as oxy (—O—) couplings.

The alkylthio-substituted TiOPc compounds of this embodiment are synthesized using a solvent-free method described in the third representative embodiment. By substantially eliminating solvent during the synthesis, production of useless byproducts such as non-metalated phthalocyanine ($H_2Pc$), that interfere with purification of the desired compounds, is prevented. This "solvent-free" synthesis is not to be confused with "solvent-processing" by which the substituted metalated phthalocyanine chromophores are formed into photovoltaically active zones of the subject devices.

In addition to providing solubility of the substituted metalated phthalocyanine molecules in solvent as used for fabricating PV devices, the alkylthio substituents also shift the Q-band absorption of the chromophore to the near-IR region, which contains many solar photons.

In this embodiment the layer of alkylthio-substituted TiOPc is formed on a coating of PEDOT:PSS (poly(3,4-ethylenedioxythiophene):polystyrenesulfonate) on indium tin oxide (ITO) formed on a glass, quartz, or other substrate 30 that is transparent to desired wavelengths of solar light. Layer formation desirably is performed in an inert atmosphere (e.g., nitrogen or noble-gas atmosphere) to exclude water and oxygen. For application, the PEDOT:PSS is dissolved and a desired molar or gravimetric ratio in a solvent to a desired concentration (e.g., 1-5% w/w) and applied at a desired thickness (e.g., 10-100 nm). PEDOT:PSS is applied using conventional techniques.

ITO is a transparent, electrically conductive oxide that forms the transparent electrode 22. ITO is a heavily doped n-type semiconductor material having a large bandgap. ITO is easily deposited as a thin film on various substrates using any of various techniques such as electron-beam evaporation, physical-vapor deposition, or sputtering. A suitable thickness range is 10-250 nm. The particular thickness is selected based on competing concerns of optical transparency and electrical conductivity, since increasing the thickness decreases the transparency of ITO and making the ITO too thin excessively reduces its conductivity. If desired or required, the ITO layer can be patterned after application using photolithography and wet-etching, for example, to form multiple devices on a substrate or to form device(s) having a desired shape and size. For convenience, ITO-coated glass is commercially available (Colorado Concepts, 120-160 nm thickness of ITO).

For application to the surface of PEDOT:PSS, a solution of the substituted metalated phthalocyanine is prepared by dissolving the compound in a suitable solvent. An example solvent is o-dichlorobenzene. Other solvents include, but are not limited to, chloroform and methylene chloride. A particular solvent is chosen not only for its ability to dissolve the chromophores but also with due consideration given to factors such as its volatility so that good-quality films of donor material can be formed using the selected film-forming technique. A good-quality film has for example a uniform arrangement of solute molecules in the film. The concentration of solute in the solution is also selected with these considerations in mind. As noted, the solution is applied by any of various layer-forming techniques, thereby forming the donor layer 18.

Figure 2A:
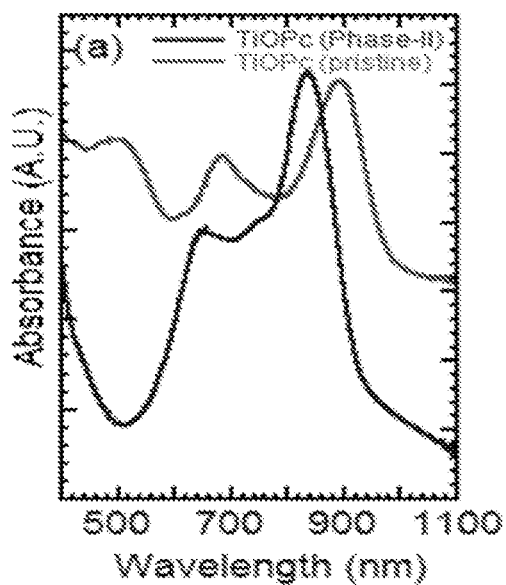
FIG. 2A is a UV-Vis-NIR spectrum of C6-TiOPc as a pristine layer.
Figure 2B:
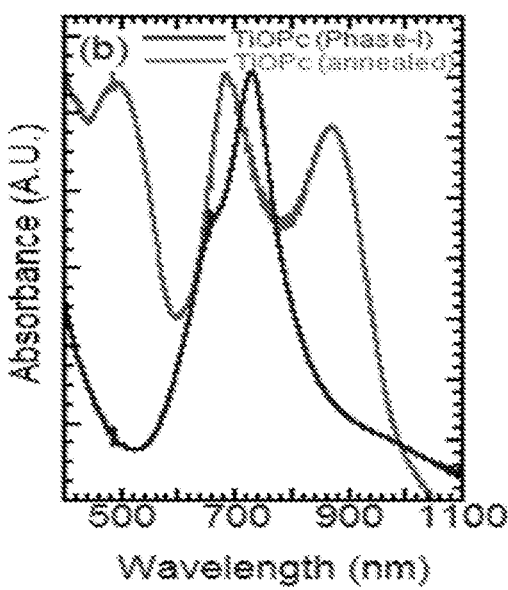
FIG. 2B is a UV-Vis-NIR spectrum of an annealed C6-TiOPc layer.

The donor layer 18 can be used unannealed (called "pristine") or annealed. Annealing serves mainly to reduce or eliminate pin-hole defects (which may form naturally in thin-films and otherwise can cause shorts between layers). Eliminating pin-hole defects tends to increase the $V_{oc}$ of the device. Also, the absorption spectrum for a pristine donor layer resembles Phase-II of unmodified TiOPc, with a Q-band maximum at approximately 892 nm (FIG. 2A). The absorption spectrum for an annealed donor layer is more like Phase-I of unmodified TiOPc, with the Q-band maximum at approximately 700 nm (FIG. 2B). Annealing tends to reduce $Q_B$, contrary to what is usually desired.

The donor-layer thickness can be optimized by adjusting operational parameters of the layer-forming technique, e.g., the speed and acceleration of a spin-coating apparatus, as well as adjusting the concentration of the solute in the solution. For example, with a spin-coating apparatus, acceleration below a setting of "225" tended to leave droplets of layer material on the surface of the thin film. A speed setting above approximately 500 rpm tended to form excessively thin, discontinuous films, and a speed setting below approximately 500 rpm tended to produce the same defects as a too-low acceleration. Layer thickness can be measured using, for example, atomic-force microscopy (AFM).

The acceptor layer 16 is formed on the donor layer 18. The acceptor material is any compound having a relatively low-lying LUMO, i.e., a compound that is easily reduced (by accepting electrons). For PHJ devices, a suitable acceptor material is $C_{60}$, one of the fullerenes. $C_{60}$ can be applied by, for example, vapor-deposition. An exemplary rate of deposition is 1-2 Å per second at a base sub-atmospheric pressure of approximately $10^{-7}$ Torr.

Figure 3:
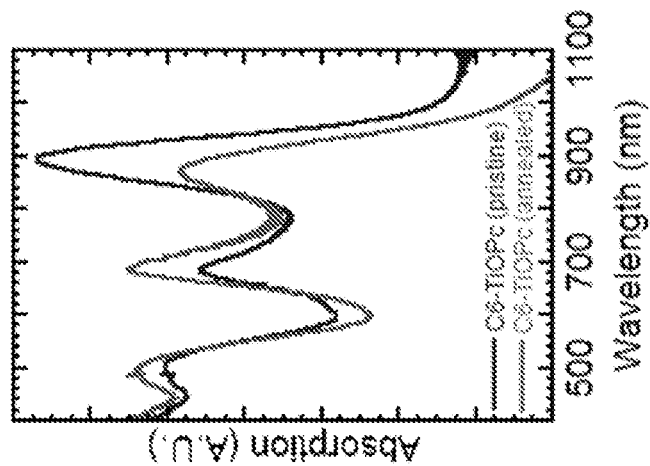
FIG. 3 depicts molecular structures of C6-TiOPc (an exemplary donor), $C_{60}$ (an exemplary acceptor), and BCP (an exemplary exciton-blocker) used in planar heterojunctions described in the first representative embodiment. The plot to the right includes respective absorbance spectra for pristine C6-TiOPc film (blue) and annealed C6-TiOPc film (red) as cast from ODCB onto PEDOT:PSS-coated ITO substrates.
Figure 3:
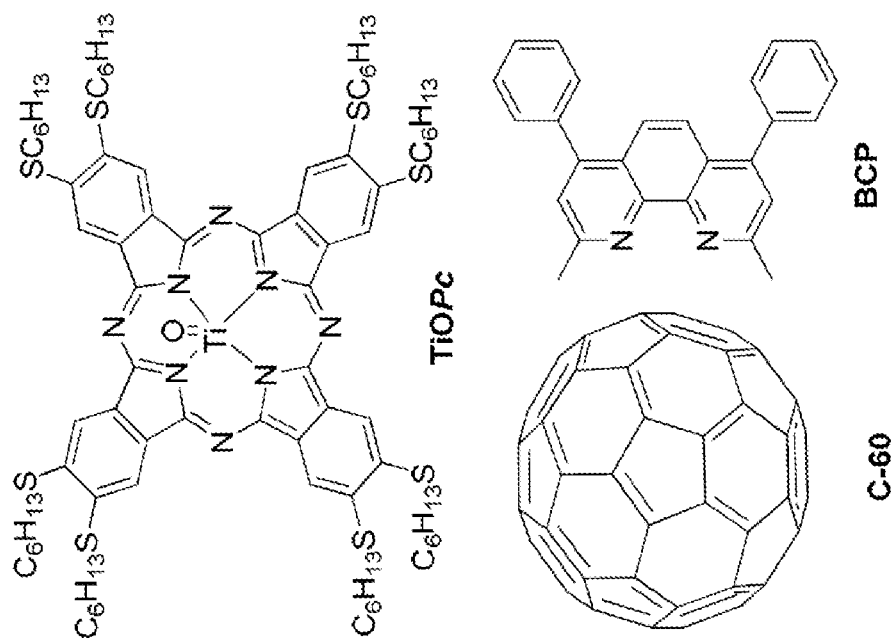

The exciton-blocking layer 14 in these PHJ devices desirably is bathocuprene ("BCP"; see FIG. 3). BCP is applied by vapor-deposition, for example, superposedly on the acceptor layer 16.

The first electrode 12 is applied superposedly (or patterned) over the layer of BCP, and desirably is a metal to provide good reflection of light incident thereof back into the cell. Example metals include, but are not limited to, aluminum, magnesium, lithium, calcium, titanium, tungsten, silver, gold, and alloys of any of these.

By way of example, pristine C6-TiOPc films (in which each substituent group is —S—$C_6H_{13}$; FIG. 3) showed two distinct peaks (FIG. 3), denoted $Q_A$ and $Q_B$, in the absorption spectrum at 680 nm and 890 nm, respectively. The $Q_B$ peak is believed to be due to the formation of charge-transfer excitons from strong intermolecular interactions between adjacent C6-TiOPc molecules. Annealing increased the amplitude of the $Q_A$ peak, but decreased the amplitude of the $Q_B$ peak and blue-shifted it by 20 nm.

By judicious selection of particular alkyl substituent groups (C5-C12, linear or branched), their coupling moieties (e.g., thio or oxy), annealing versus no annealing, solvent used in solvent-processing, manner of forming thin-films, and the like, photovoltaically active layers in OPV devices according to this embodiment can have "tuned"

photosensitivity. In other words, the photosensitivity can be tuned to specific desired wavelengths in the near-IR and visible bands.

Example 1

In this example, four OPV PHJ devices according to the first representative embodiment were fabricated; two with pristine C6-TiOPc donor layers (devices 1 and 3), and two with annealed C6-TiOPc donor layers (devices 2 and 4). The device configuration was as follows: ITO/PEDOT:PSS/C6-TiOPc/$C_{60}$/BCP/Al. Device area=0.019 cm². Thickness of PEDOT:PSS layer=108 nm. Exemplary device parameters are set forth in Table 2.

TABLE 2

| Dev | l (nm) | $V_{OC}$ (V) | $J_{SC}$ (mA/cm²) | FF | $R_S$ | $R_P$ | $J_0$ | η |
|---|---|---|---|---|---|---|---|---|
| 1 | 21 | 0.39 | 3.17 | 0.40 | 0.810 | $1.04 \times 10^2$ | $3.54 \times 10^{-4}$ | 0.78% |
| 2 | 23 | 0.49 | 2.10 | 0.34 | 2.24 | $3.36 \times 10^3$ | $1.89 \times 10^{-4}$ | 0.53% |
| 3 | 28 | 0.35 | 3.29 | 0.55 | 0.80 | $1.96 \times 10^3$ | $3.36 \times 10^{-4}$ | 0.97% |
| 4 | 34 | 0.40 | 2.15 | 0.50 | 1.10 | $1.72 \times 10^3$ | $2.11 \times 10^{-4}$ | 0.66% |

In Table 2, devices 1 and 3 had pristine films (C6-TiOPc/PEDOT:PSS/ITO), and devices 2 and 4 had films that were annealed (150° C. for 10 minutes) prior to vacuum-deposition of the BCP layer. In the table, l is the thickness of the donor layer (in nm); $V_{oc}$ is open-circuit photo-potential; $J_{sc}$ is photo-current; FF is fill factor, $R_s$ is series resistance as measured from far-forward bias; $R_p$ is shunt resistance as measured from far-reverse bias; $J_0$ is reverse saturation current as estimated from lowest dark current (log plot); and η is power-conversion efficiency. $J_{sc}$ (photo-current) is the maximum current delivered by the cell through a load under short-circuit conditions. FF (fill factor) is the ratio of maximum power ($V_{mc} \times J_{mp}$) divided by $J_{sc}$ and $V_{oc}$. The power-conversion efficiency η is derived from the equation: $\eta = (J_{sc} V_{oc} FF)/P_o$, in which $P_o$ is incident-light intensity (65.5 mW/cm²).

Figure 4A:
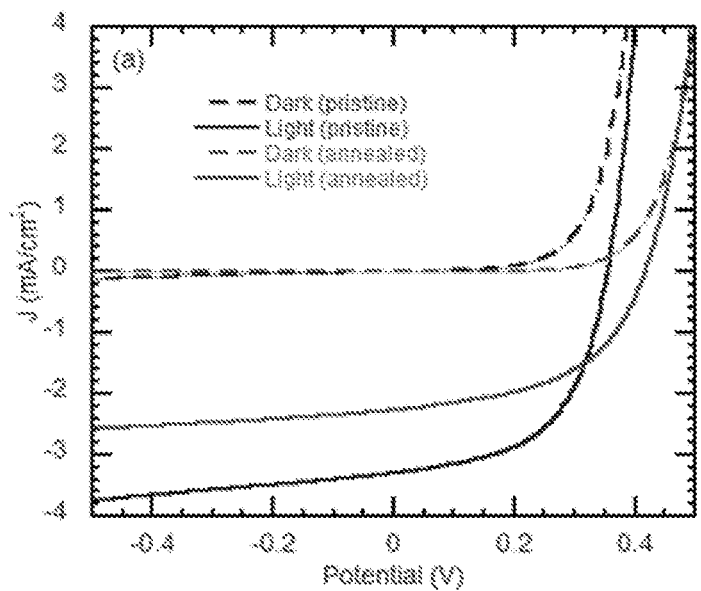
FIG. 4A is a linear J-V plot (performance) of OPV device 3, either pristine or annealed, illuminated at 65.5 mW·cm$^{-2}$ or dark, as discussed in the first example.
Figure 4B:
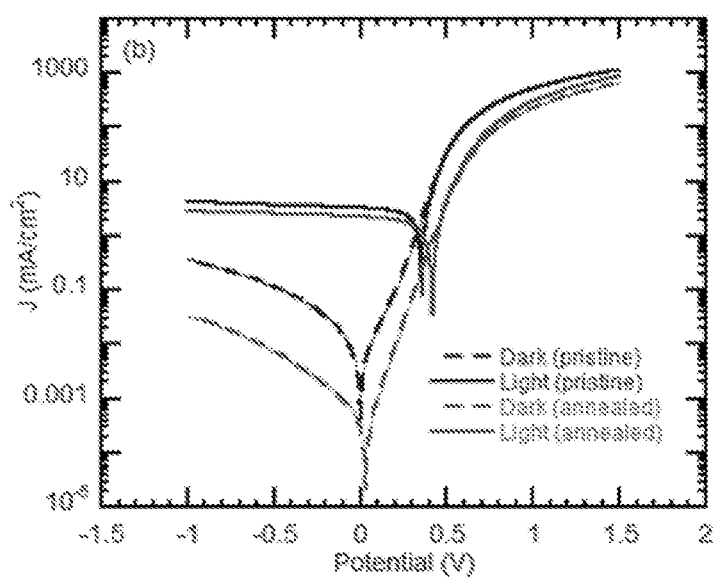
FIG. 4B is a semi-log J-V plot (performance) of OPV device 3, either pristine or annealed, illuminated at 65.5 mW·cm$^{-2}$ or dark, as discussed in the first example.

Device 1, having a donor-layer thickness of approximately 21 nm exhibited a $V_{oc}$ and a $J_{sc}$ of 0.39 V and 3.17 mA/cm², respectively, with a η of 0.78% (FIGS. 4A and 4B, in which FIG. 4A is a linear J-V plot and FIG. 4B is a semi-logarithmic J-V plot). Upon increasing the donor-layer thickness to 28 nm, the $V_{oc}$ decreased to 0.35 V while a slight increase in $J_{sc}$ to 3.29 mA/cm² was observed for device 3. The increased fill factor for device 3 (0.55), compared to device 1 (0.40), is responsible for the corresponding increase in efficiency (0.78%→0.97%). The annealed devices 2, 4 exhibited lower $J_{sc}$, and FF but higher $V_{oc}$ values than their unannealed counterparts. This behavior is consistent with planarization of the C6-TiOPc film during thermal annealing that decreases the interfacial surface area between the C6-TiOPc donor and the $C_{60}$ acceptor, thereby decreasing the current. The increase in photopotential is likely due to a reduction in pinholes, further evidenced by the lower reverse saturation current. Reduced performance of the annealed devices 2, 4 exhibiting decreased $Q_B$ (but increased $Q_A$) bands indicates higher photo-activity for the $Q_B$ band.

Figure 5A:
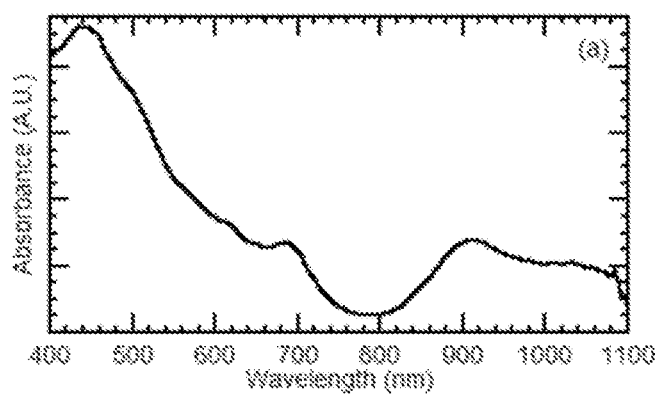
FIG. 5A is a Vis-NIR absorption spectrum for OPV device 3 discussed in the first example, illuminated at 100 mW·cm$^{-2}$.
Figure 5B:
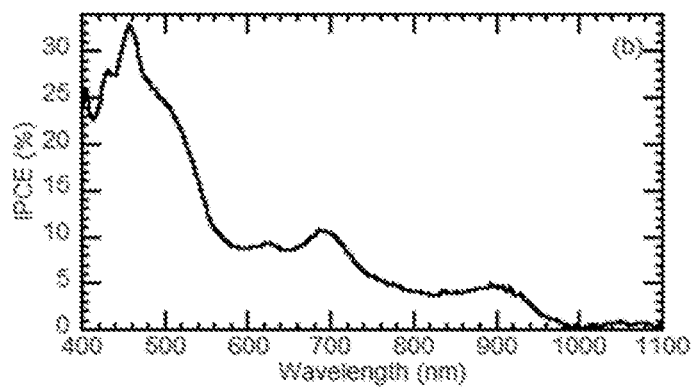
FIG. 5B is a plot of incident photon to current efficiency (IPCE) for OPV device 3 discussed in the first example, illuminated at 100 mW·cm$^{-2}$.
Figure 5C:
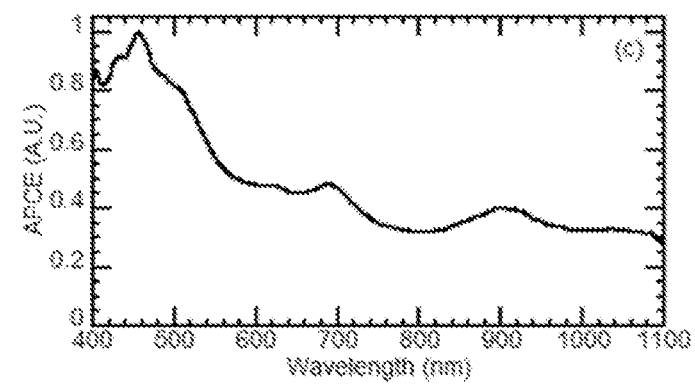
FIG. 5C is a plot of absorbed photon to current efficiency (ACPE) for OPV device 3 discussed in the first example, illuminated at 100 mW·cm$^{-2}$.
Figure 6A:
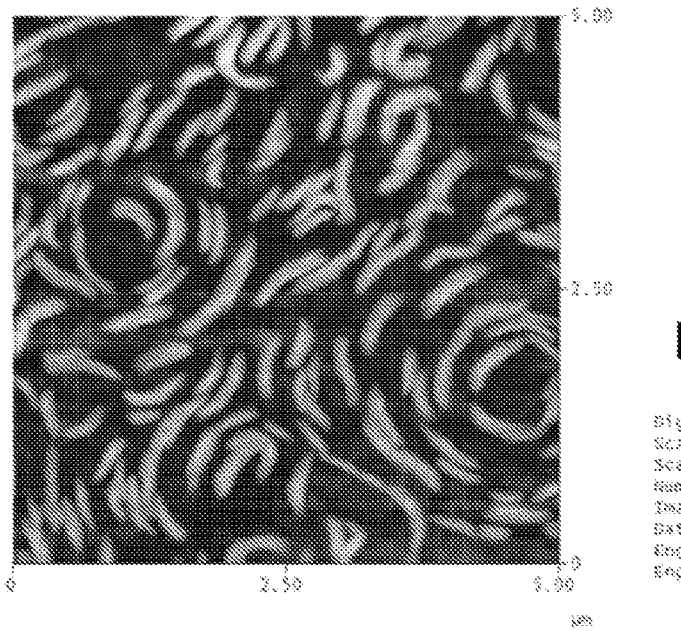
FIGS. 6A-6D are respective AFM height images for the active layer of each of devices 1-4, respectively, as discussed in the first example.
Figure 6A:
Figure 6B:
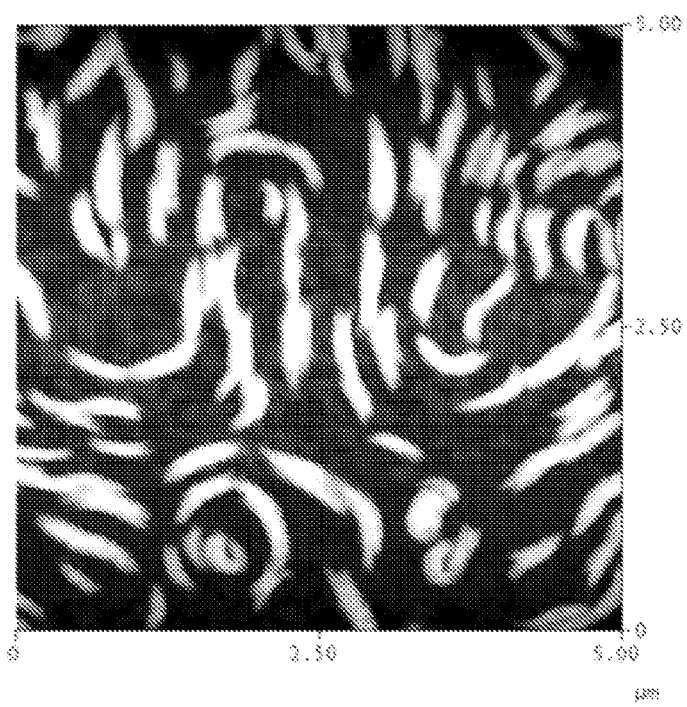
Figure 6B:
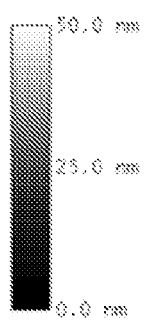
Figure 6C:
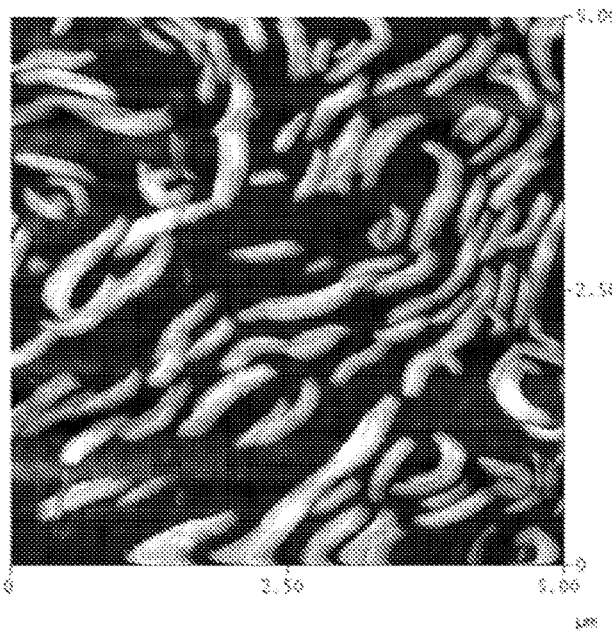
Figure 6C:
Figure 6D:
Figure 6D:
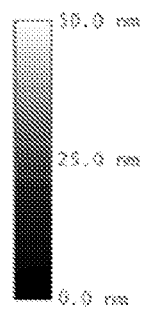

Quantum-efficiency measurements were performed on the best-performing device, namely device 3. The absorbance spectrum for device 3 exhibited a panchromatic absorption extending up to 1 μm in the near-IR, which is an overlay of the $C_{60}$ absorption band around 400-600 nm and the C6-TiOPc $Q_A$-band and $Q_B$-band absorptions from 600-1000 nm (FIGS. 5A-5C). IPCE measurements were performed on a similar device, having an area 0.125 cm², inside a sealed stainless steel vessel in a nitrogen or other inert atmosphere. APCE data were determined from the IPCE data and the absorbance (transmittance) spectrum for the device along the transparent region near the device. The APCE spectrum directly correlated with the corresponding IPCE spectrum, with the maximum absorbed and incident photon-to-electron conversion being approximately 450 (corresponding to $C_{60}$, consistent with its higher absorbance in the device). The APCE/IPCE spectra revealed contributions from the C6-TiOPc in the near-IR region, with local maxima being approximately 680 nm and 920 nm, corresponding to the $Q_A$ and $Q_B$ bands of the C6-TiOPc. The lower contributions from the C6-TiOPc $Q_A$ and $Q_B$ bands toward the IPCE/APCE spectra suggest recombination of excitons.

Atomic-force microscopy (AFM) images of the surfaces of the active layers of devices 1-4 are provided in FIGS. 6A-6D, which reveal multiple, discrete domains.

This example demonstrated that the photo-activity of PHJ OPV devices can be extended up to 1 μm in the near-IR region of the solar spectrum, without compromising the $V_{oc}$, using solution-processed alkylthio-substituted TiOPc as the donor layer.

Experimental protocols for this example were as follows:

Substrate Preparation for High-Throughput Testing of OPV Devices:

ITO-coated glass (sheet resistance: ~15 Ω·cm⁻²) was pretreated by scrubbing with 10% Triton-X100 using a micro-fiber cloth, followed by successive sonications in 10% Triton-X100 (15 min), nanopure water (5 min), and absolute ethanol (15 min). The substrates were then dried under a stream of nitrogen.

Substrate Preparation for Analytical Testing of OPV Devices:

The surface of ITO-coated glass (sheet resistance ~15 Ω·cm⁻²) was flooded with a positive photoresist (Rohm and Hass) and spun at 2000 RPM for 30 seconds to achieve spin-coating. A shadow mask was used to pattern the ITO with individual discrete device loci, followed by development of the ITO pattern. Aqua Regia (3:1) was pre-heated to 120° C., in which the resist-coated ITO glass slides were immersed for 35 seconds. Then the photoresist was removed. The ITO was then pretreated by scrubbing with 10% Triton-X100 using a micro-fiber cloth, followed by successive sonications in 10% Triton-X100 (15 min), nanopure water (5 min), and absolute ethanol (15 min). The substrates were then dried under a stream of nitrogen.

Device Fabrication:

A solution of PEDOT:PSS (1.4% (w/w), CLEVIOS™) was passed through a 0.45-micron filter before flooding the ITO surfaces with 1 mL each of the solution. The ITO substrates were then spun at 3000 rpm (acceleration set to 225) for 1 minute to spin-coat. The slides were transferred to a glove box in which they were annealed at 175° C. (on a pre-equilibrated hot plate). The slides were then allowed to cool to room temperature. Annealing the C6-TiOPc/PEDOT/ITO substrates was performed at 150° C. for 10 min, as required. $C_{60}$ (MER Corp.) and bathocuproine ("BCP," Sigma-Aldrich) were successively vacuum-deposited (approximately 1-2 Å·sec$^{-1}$) superposedly on the C6-TiOPc layers at a base pressure of approximately 10$^{-7}$ Torr using Knudsen-type sublimation cells. Monitoring was performed using a 10-MHz quartz-crystal microbalance (QCM-Newark) and an Agilent Technologies frequency monitor (Model 53131A). Aluminum was deposited (approximately 1-3 Å·sec$^{-1}$) at a base pressure of approximately 10$^{-6}$ Torr and monitored using a 6-MHz QCM (Tangidyne) and Inficon deposition monitor (model 758-500-G1). The region at the center of these substrates was left open to allow for absorbance spectra to be measured on the same films for which IPCE data was obtained.

Device Testing:

Current density-voltage (J-V) data were obtained from devices each having a surface area of 0.019 cm$^2$. IPCE data were obtained from devices having a surface area of 0.125 cm$^2$. The devices were tested inside a glove-box under ambient nitrogen pressure. Current density-voltage (J-V) measurements were made using a Keithley 2400 source meter, and the respective data were acquired using software created using Labview ver. 8.2 (National Instruments). Devices were scanned from −1.00 to +1.50 Volts with a 5-mV step size, starting from negative bias. A 250-W quartz-halogen lamp was used as an illumination source. The light was filtered with a 950-nm cut-off filter along with a sand-blasted light diffuser. The distance between the source and the devices was adjusted to achieve an output of approximately 66 mW·cm$^{-2}$, which was measured using a Newport thermopile photodetector (Model 818P-015-19).

Second Representative Embodiment

This embodiment is directed to solution-processed bulk heterojunction (BHJ) organic photovoltaic (OPV) devices in which a soluble alkylthio-substituted titanyl phthalocyanine (TiOPc) is used as the electron donor. These devices exhibit photoactivity to incident wavelengths up to 1 μm (in the near-IR region of the solar spectrum), without significantly affecting the open-circuit photopotential ($V_{oc}$) of the device.

The BHJs of these OPV devices are fabricated by solution-processing, resulting in formation of thin-films on substrates that can be rigid or flexible, as discussed in the first representative embodiment. The substrates can be any size, and the size of devices is scalable without limitation. Film formation can be achieved using any convenient method by which liquids can be formed into films on a substrate, such as but not limited to reel-to-reel wet coating, ink-jet printing, and spin-coating.

BHJ OPV devices according to this embodiment comprise alkylthio-substituted metalated phthalocyanines as described in the first representative embodiment. An example such compound is octahexylthio-substituted TiOPc (C6-TiOPc). The alkylthio-substituted TiOPc was synthesized using a solvent-free method as disclosed in the third representative embodiment. As discussed in the first representative embodiment, the alkylthio substituents are effective because they: (a) shift the Q-band absorption of the donor to include the near-IR region, (b) impart solubility of the donor in common organic solvents, and (c) promote secondary sulfur-sulfur non-covalent interactions. Polymorphs of the particular alkylthio-substituted TiOPc with different respective near-IR absorptivities can be obtained. These compounds exhibit absorption spectra reminiscent of Phase-I of unmodified TiOPc, with two distinct peaks ($Q_A$ and $Q_B$) in the absorption spectrum at 695 nm and 874 nm, respectively (FIG. 7). The $Q_B$ peak is believed to be due to the formation of charge-transfer excitons due to strong intermolecular interactions between individual TiOPc chromophore molecules. Molecular arrangement in the condensed phase of TiOPc arises from a combination of strong interactions between the Ti=O bonds and strong π·π interactions, which is important for absorption in the near-IR.

A schematic diagram of an OPV device 40 according to this embodiment is shown in FIG. 1B. The device 40 comprises a first electrode 42, an exciton-blocking layer 44, a BHJ active layer 46, an optional PEDOT:PSS layer 48, and a transparent electrode 50 (e.g., ITO). The first electrode 42 is substantially as described above in the first embodiment. The surface of the first electrode as formed can be coated with a layer of LiF as an EBL for the BHJ 46. The transparent electrode 50 is as described above in the first representative embodiment. The active layer 46, comprising the BHJ, is a mixture of alkylthio-substituted TiOPc and a suitable acceptor. A particularly useful acceptor for use in forming the BHJ is phenyl $C_{61}$ butyric acid methyl ester (PCBM), which is a fullerene with a "tail" that facilitates solubility of the compound.

The BHJ is prepared by blending the substituted TiOPc chromophore (as electron donor; in solution with the solvent) with the acceptor (FIG. 7). The donor and acceptor are immiscible, so blending includes sufficient agitation to form a suspension of extremely fine (in the 10-nm range) units of donor and acceptor. The suspension is layered on the PEDOT:PSS layer 48 using substantially any desired layer-forming technique. Upon evaporation of the solvent, the resulting BHJ layer 46 exhibits absorption extending up to 1000 nm with a band at approximately 400 nm, typical of PCBM. By way of example, C6-TiOPc as donor exhibits $Q_A$ and $Q_B$ bands at approximately 690 nm and 875 nm, respectively. Since the $Q_A$ and $Q_B$ peaks are similar to those observed in pristine, unblended films of the respective alkylthio-substituted TiOPc film, the PCBM acceptor molecules in the BHJ layer 46 apparently do not significantly disrupt intermolecular interactions in the donor molecules.

The exciton-blocking layer 44 in this embodiment is a very thin film of LiF. LiF in BHJ OPV devices is believed to perform the following: (a) form an ohmic contact with fullerene acceptors, (b) protect the active layer from hot atoms of the metal used to form the first electrode 42 (e.g., aluminum) by thermal deposition, (c) dope the organic material beneath the first electrode, thereby increasing $V_{oc}$ in some devices, (d) establish a dipole that influences charge-carrier extraction, and (e) slightly alter the effective work function of metals such as aluminum used to form the first electrode.

In exemplary experiments BHJ active layers 46 of different thicknesses were prepared by spin-coating solutions of C6-TiOPc and PCBM of varying respective concentrations on glass substrates. The morphology of the BHJ layers was dependent on the ratio of donor to acceptor in the BHJs. Morphology was assessed by atomic force microscopy (AFM). By way of example, a BHJ layer 46 comprising a C6-TiOPc:PCBM ratio of 1:1 (w/w) had large, spherical domains (FIG. 8A) of diameter approximately 450 nm and rms surface roughness of 8 nm. In contrast, BHJ layers 46 formed from a C6-TiOPc/PCBM ratio of 1:3 (w/w) were relatively smooth as desired, without large domains (FIG.

8B; note scale difference from FIG. 8A). The pattern of the phase-segregations was independent of BHJ film thickness.

Example 2

This example exemplifies the second representative embodiment. Six BHJ OPV devices were fabricated by spin-coating, under ambient atmosphere, respective solutions of C6-TiOPc/PCBM in $CHCl_3$ onto respective layers of PEDOT:PSS (112-nm thick) applied to clean ITO-coated glass substrates. The BHJ layer 46 was dried under ambient atmosphere and then moved to a glove box. LiF (0.12 nm thickness, 0.2 Å/sec deposition rate) and aluminum (100 nm thickness, 0.9-1.2 Å/sec deposition rate) were deposited in sequence under vacuum (approximately $10^{-6}$ Torr) to complete the devices.

Six devices were fabricated, denoted devices 1-6, respectively. Device 1 of this example had an active layer 46 of approximately 31-nm thickness ("d") and comprised C6-TiOPc/PCBM at a ratio of 1:1 (w/w). This device exhibited a relatively low $V_{oc}$ of 0.17 mV, which indicated the presence of pin-holes in the relatively thin active layer 46. Device 2 had an active-layer thickness d=40 nm, which produced an increase in $J_{sc}$, $V_{oc}$, and FF compared to device 1 (Table 3). A further increase in active-layer thickness to 72 nm (device 3) decreased $J_{sc}$, $V_{oc}$, and FF, indicating that, in this device, the thickness of the active layer 46 exceeded the exciton-diffusion length. The $V_{oc}$=0.54 mV for device 2 is comparable to the $V_{oc}$=0.55 mV for an optimized PHJ device fabricated from solution-processed C6-TiOPc. Changing the C6-TiOPc/PCBM ratio from 1:1 (w/w) to 3:1 yielded a poor device. However, in device 4 having a TiOPc:PCBM ratio of 1:3 (w/w) in a 91-nm thick active layer 46, a significant increase in both $V_{oc}$ and $J_{sc}$ to 0.65 mV and 1.0 mA, respectively, was observed (Table 3). Further increasing the active-layer thickness to 121 nm in device 5 increased $V_{oc}$, but $J_{sc}$ and FF decreased significantly, indicating limited charge mobility (Table 3). The $V_{oc}$ for device 5 at 0.65 mV is comparable to the $V_{oc}$ (0.61 mV) of a PHJ device fabricated from vacuum-deposited TiOPc (Example 1).

Figure 9A:
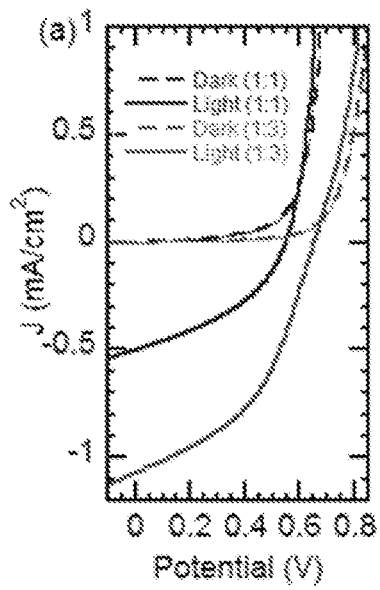
FIGS. 9A and 9B are linear and semilog plots, respectively, of J-V data from C6-TiOPc/PCBM BHJ OPV device 2 (blue) and device 5 (red) in the dark (dashed line) and under illumination (solid line), as described in the second example.
Figure 9B:
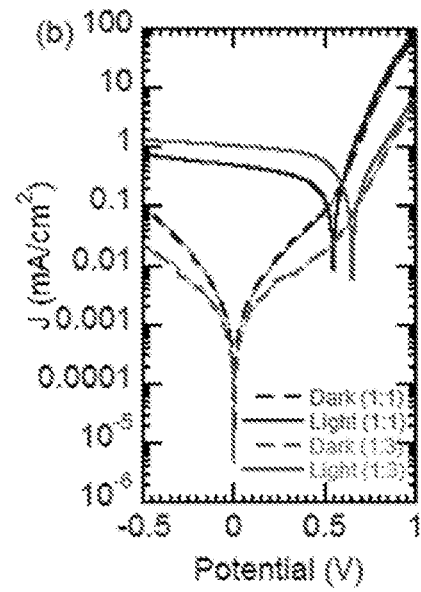

In device 6, the active layer 46 was annealed, which produced a significant reduction in the $V_{oc}$ (Table 3). Hence, a balance between optical absorption and charge recombination was achieved by devices having active-layer thicknesses of 40 and 91 nm and C6-TiOPc/PCBM ratios of 1:1 and 1:3, respectively. The J-V and semi-log plot for the best-performing devices 2 and 5 are shown in FIGS. 9A and 9B. The lower performance of devices 1 and 3 may be the result of unfavorably large domains of C6-TiOPc being formed in their active layers, which can serve as sites for recombination (FIG. 9B).

TABLE 3

| Device | Ratio | Conc. (mg/mL), d (nm) | $V_{oc}$ (V) | $J_{sc}$ (mA · cm²) | FF | η |
|---|---|---|---|---|---|---|
| 1 | 1:1 | 6, 31 | 0.168 | 0.330 | 0.312 | 0.017 |
| 2 | 1:1 | 12, 40 | 0.547 | 0.500 | 0.404 | 0.110 |
| 3 | 1:1 | 18, 72 | 0.380 | 0.288 | 0.353 | 0.038 |
| 4 | 1:3 | 12, 91 | 0.651 | 1.074 | 0.449 | 0.314 |
| 5 | 1:3 | 18, 121 | 0.711 | 0.457 | 0.258 | 0.083 |
| 6 | 1:3 | 18, 149 | 0.414 | 0.467 | 0.358 | 0.083 |

The devices 1-6 had the following general configuration: ITO/PEDOT:PSS/C6-TiOPc:PCBM/LiF/Al with device area of 0.019 cm². The thickness of the PEDOT:PSS layer was 112 nm. In the table, η, $J_{sc}$, $V_{oc}$, FF, and $P_o$ are as defined in Table 2. Incident-light intensity was 65.5 mW/cm². The "ratio" column is the ratio of C6-TiOPc to PCBM in the blend used to form the active layer. d is the thickness of the active layer. The active layer in device 6 was annealed at 150° C. for 10 min.

Figure 10A:
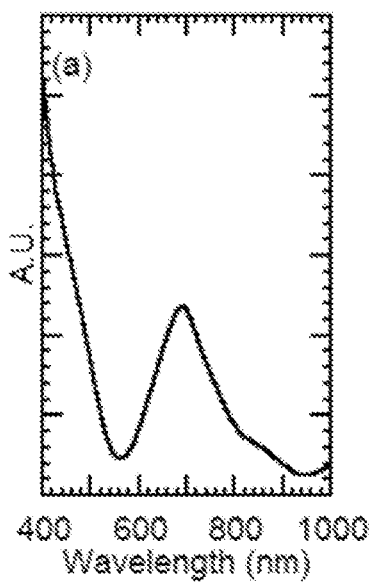
FIGS. 10A, 10B, and 10C are plots of absorbance, IPCE, and APCE, respectively, for OPV device 4, as described in the second example.
Figure 10B:
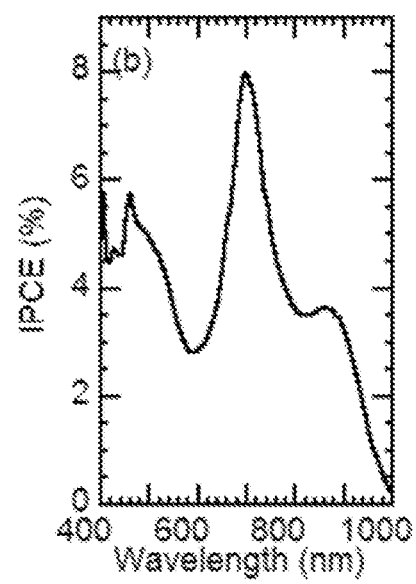
Figure 10C:
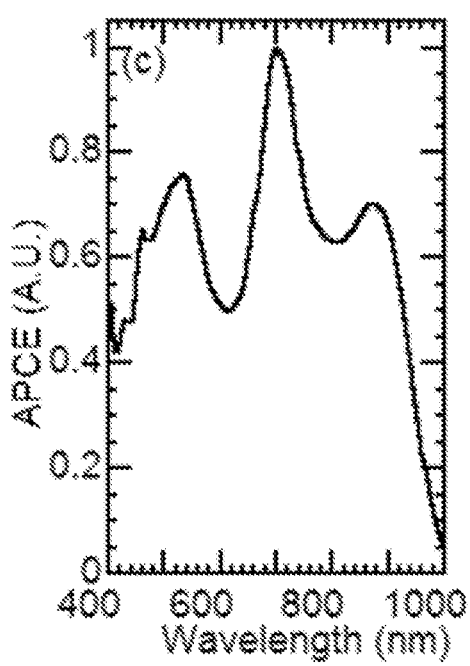

IPCE measurements of the devices were conducted under ambient atmosphere at AM1.5G to determine the best-performing device. Corresponding APCE data were calculated from the IPCE data and the absorbance (transmittance) spectra for the devices along the transparent region near the devices. The respective shapes of the IPCE curves and the device-absorption spectra were significantly different; for example, see FIGS. 10A-10C pertaining to device 4. FIG. 10A is an absorbance spectrum; FIG. 10B is a plot of IPCE, and FIG. 10C is a plot of ACPE. The absorbance spectrum of this device showed a higher contribution from PCBM than from C6-TiOPc (FIG. 10A). However, the relative contributions to the IPCE from TiOPc exceeded that of PCBM, suggesting that incident photons are more efficiently converted to electrons by the C6-TiOPc compared to PCBM. Although the $Q_B$ band of C6-TiOPc is indistinct in the absorption spectrum (FIG. 10A), a significant contribution from this band toward the IPCE was observed (FIG. 10B). The APCE spectrum (FIG. 10C) directly correlated with the corresponding absorption spectrum of a pristine C6-TiOPc layer, with the maximum APCE at approximately 700 nm corresponding to the $Q_A$ band of C6-TiOPc. The APCE spectrum also revealed a significant contribution from the $Q_B$ band of C6-TiOPc $Q_B$ band in the near-IR region with a local maximum around 870 nm.

Figure 16A:
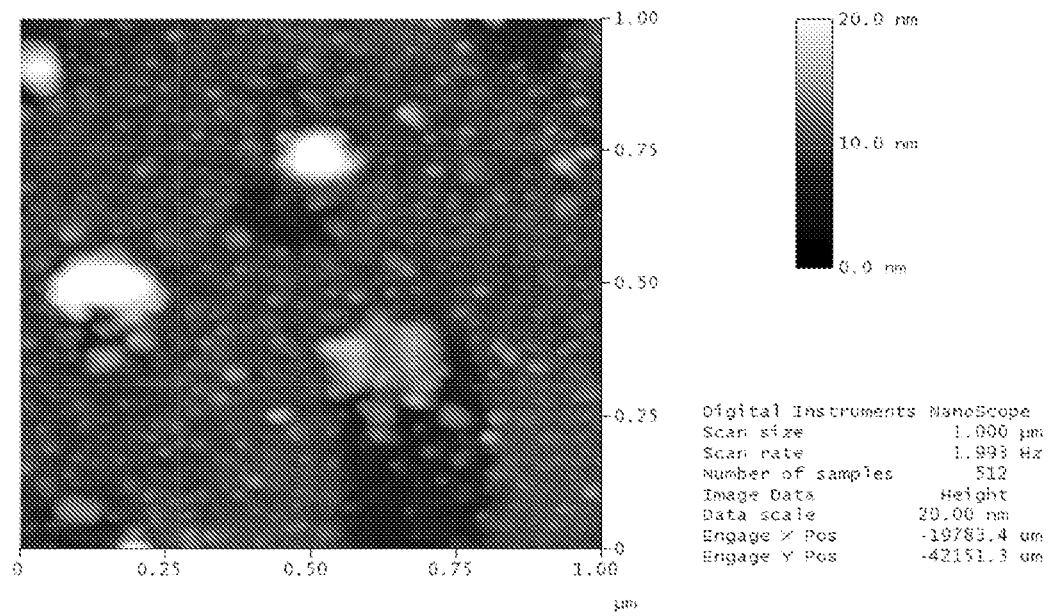
FIGS. 16A-16F are respective AFM height images for thin-films prepared from different ratios and concentrations of C6-TiOPc and PCBM on PEDOT:PSS-coated ITO substrates.
Figure 16B:
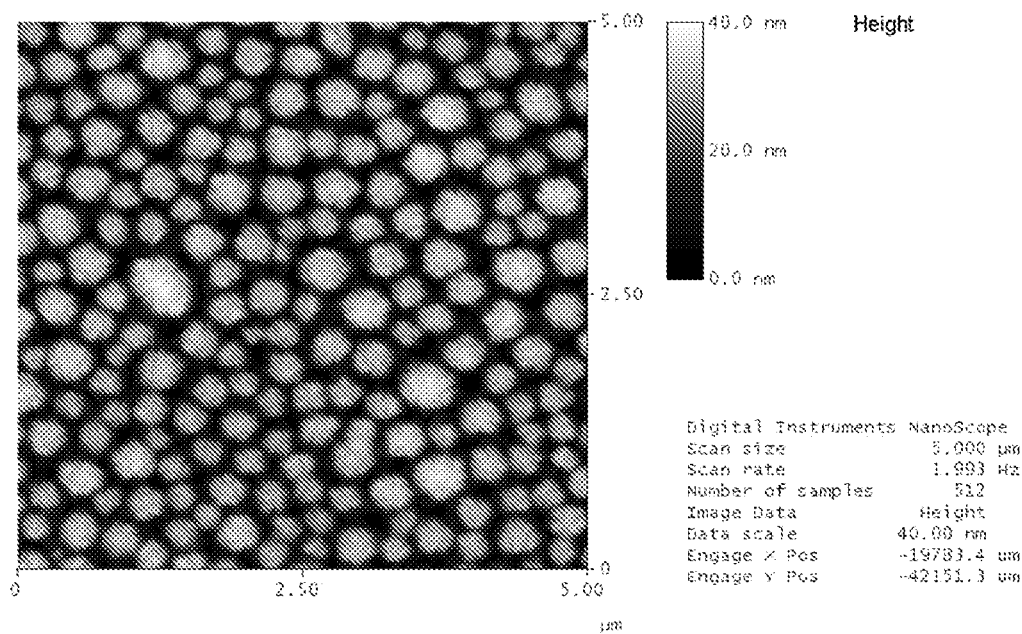
Figure 16C:
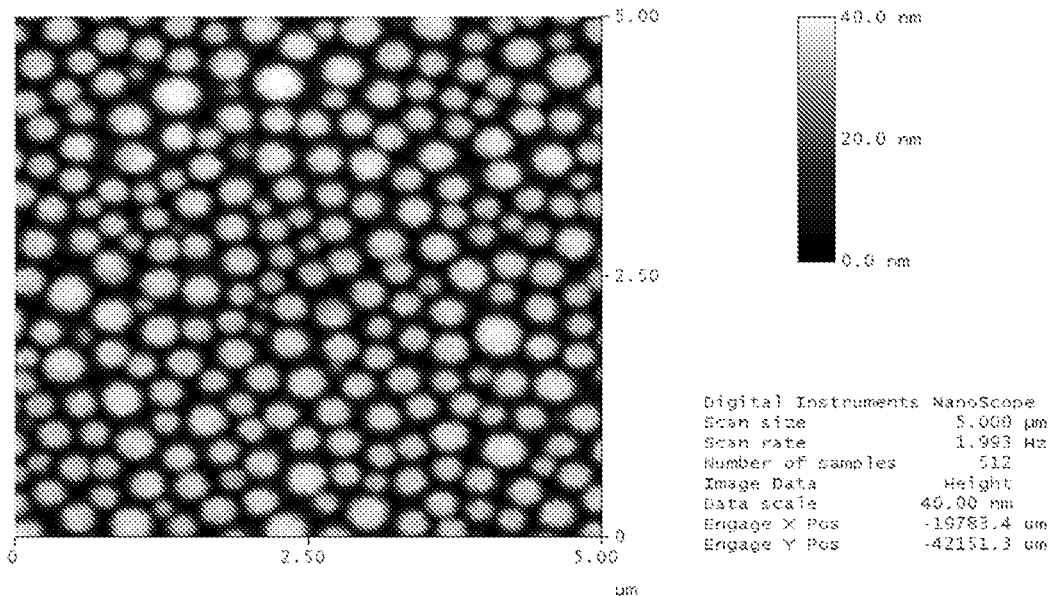
Figure 16D:
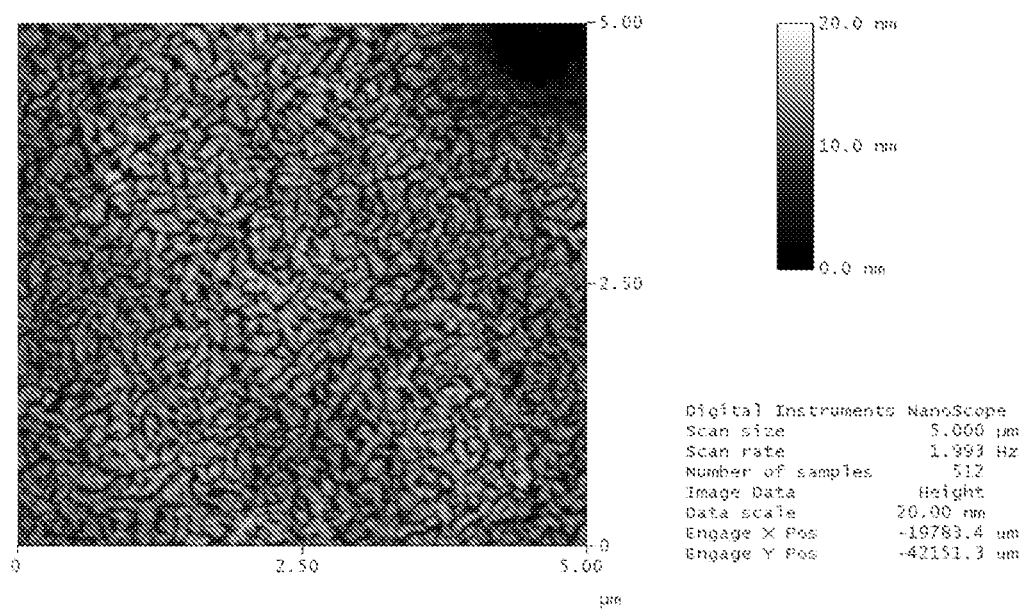
Figure 16E:
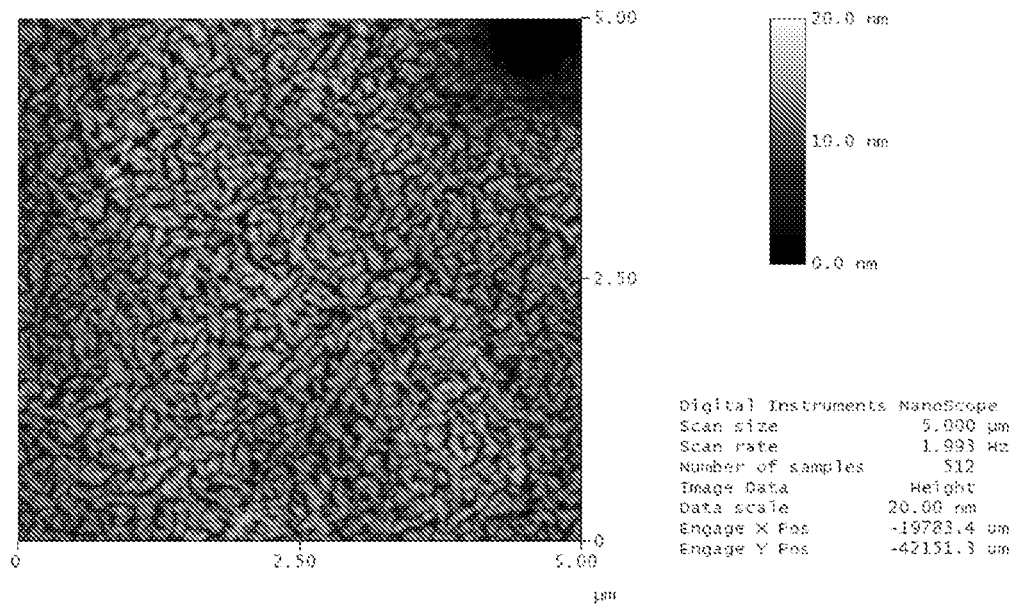
Figure 16F:
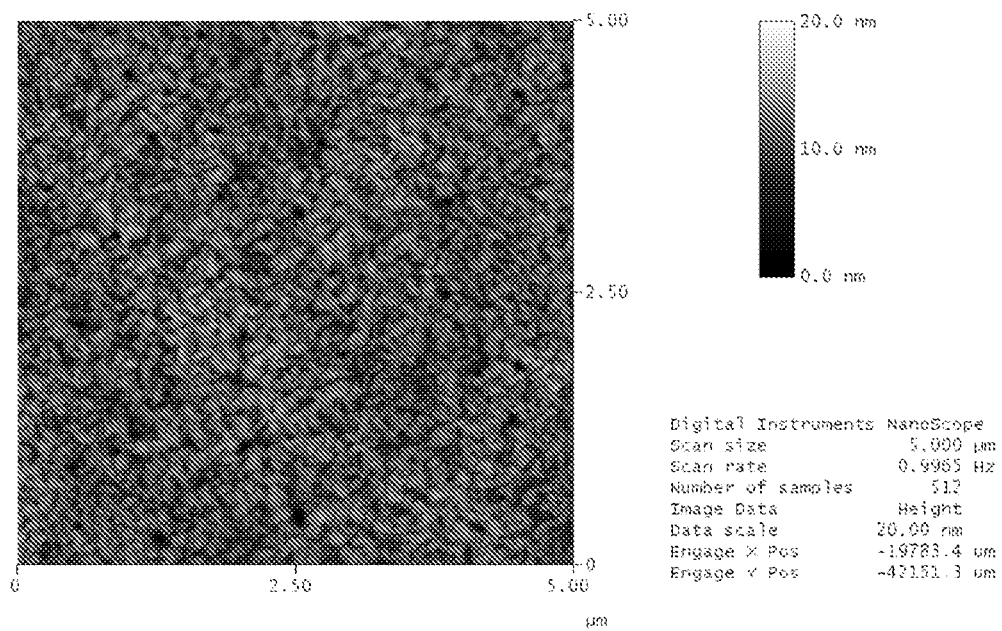

Atomic-force microscopy (AFM) images were obtained of the surfaces of devices 1-6 and are shown in FIGS. 16A-16F, respectively. Note the smooth domains in FIGS. 16D-16F, compared to the crystallite-like domains in FIGS. 16B-16C.

This example demonstrated good near-IR photoactivity for solution-processed BHJ OPV devices. With the optimized devices, the $V_{oc}$ is higher than with corresponding solution-processed PHJ devices comprising octahexylthio-substituted C6-TiOPc. The $V_{oc}$ was comparable to the vacuum-deposited PHJ fabricated from Phase-I of non-substituted TiOPc.

Third Representative Embodiment

This embodiment is directed to a general method for the synthesis of any of various metalated-phthalocyanines having alkyl chalcogenide ring substituents. We have used this general synthesis method to produce, for example, soluble alkylthio-substituted TiOPcs having alkylthioethers (AT; —S—R, where R is alkyl) at peripheral (β) positions as substituent groups. The general method eliminates formation, during synthesis of the desired product, of $H_2Pc$ byproducts that otherwise make purification of the desired product difficult. The alkylthioether (AT) side chains (i.e., —S—R side chains) enhance processability of the desired product and provide a way in which to tune the optical and photovoltaic properties of the product when used in thin-films, such as photovoltaically active thin-films. Thin-films of various AT-TiOPc products disclosed here exhibit near-IR absorption substantially the same as vacuum-deposited non-substituted Phase-II TiOPc. The products also exhibit an additional red-shifted Q-band due to the presence of the thioether groups at the β-positions. This embodiment also provides a simple route to various polymorphs whose optical properties are reminiscent of Phase-I and Phase-II crystalline polymorphs. This route is made possible through choice of substituent chain lengths and processing solvents.

An example of the general synthetic method is described below with reference to the following reaction diagram:

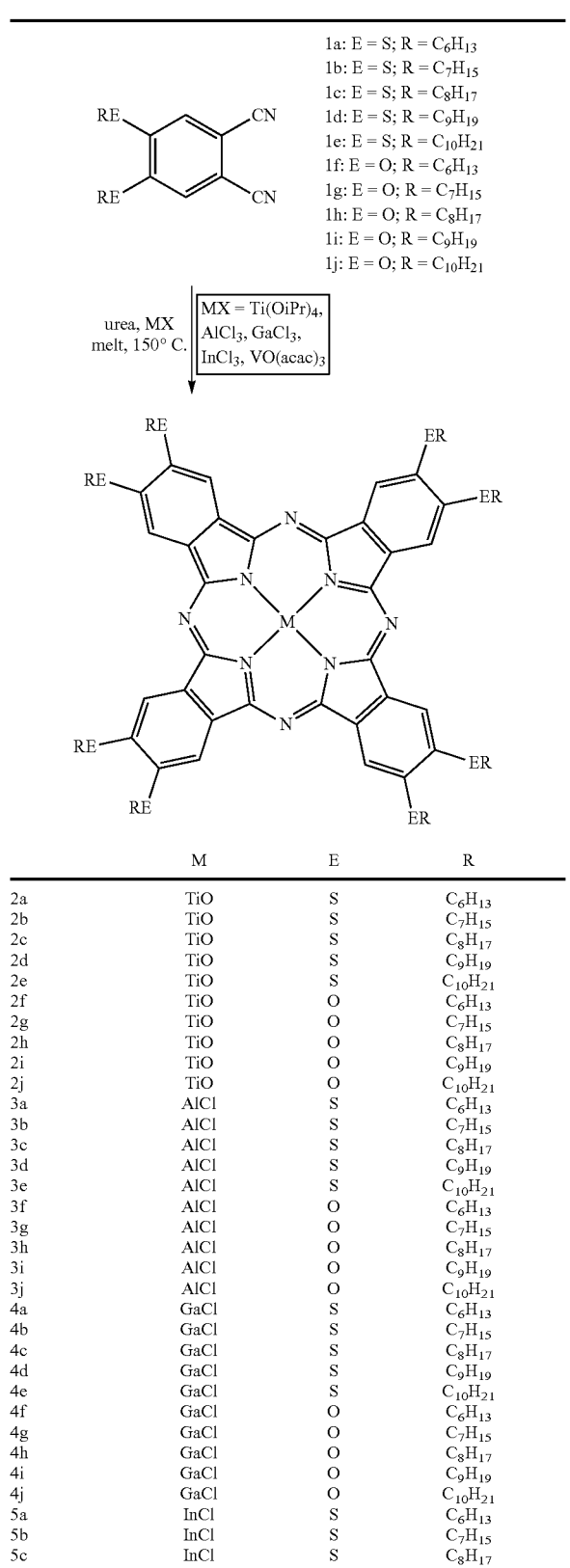

1a: E = S; R = $C_6H_{13}$
1b: E = S; R = $C_7H_{15}$
1c: E = S; R = $C_8H_{17}$
1d: E = S; R = $C_9H_{19}$
1e: E = S; R = $C_{10}H_{21}$
1f: E = O; R = $C_6H_{13}$
1g: E = O; R = $C_7H_{15}$
1h: E = O; R = $C_8H_{17}$
1i: E = O; R = $C_9H_{19}$
1j: E = O; R = $C_{10}H_{21}$ urea, MX melt, 150° C.
MX = Ti(OiPr)$_4$, AlCl$_3$, GaCl$_3$, InCl$_3$, VO(acac)$_3$

|    | M    | E | R           |
|----|------|---|-------------|
| 2a | TiO  | S | $C_6H_{13}$ |
| 2b | TiO  | S | $C_7H_{15}$ |
| 2c | TiO  | S | $C_8H_{17}$ |
| 2d | TiO  | S | $C_9H_{19}$ |
| 2e | TiO  | S | $C_{10}H_{21}$ |
| 2f | TiO  | O | $C_6H_{13}$ |
| 2g | TiO  | O | $C_7H_{15}$ |
| 2h | TiO  | O | $C_8H_{17}$ |
| 2i | TiO  | O | $C_9H_{19}$ |
| 2j | TiO  | O | $C_{10}H_{21}$ |
| 3a | AlCl | S | $C_6H_{13}$ |
| 3b | AlCl | S | $C_7H_{15}$ |
| 3c | AlCl | S | $C_8H_{17}$ |
| 3d | AlCl | S | $C_9H_{19}$ |
| 3e | AlCl | S | $C_{10}H_{21}$ |
| 3f | AlCl | O | $C_6H_{13}$ |
| 3g | AlCl | O | $C_7H_{15}$ |
| 3h | AlCl | O | $C_8H_{17}$ |
| 3i | AlCl | O | $C_9H_{19}$ |
| 3j | AlCl | O | $C_{10}H_{21}$ |
| 4a | GaCl | S | $C_6H_{13}$ |
| 4b | GaCl | S | $C_7H_{15}$ |
| 4c | GaCl | S | $C_8H_{17}$ |
| 4d | GaCl | S | $C_9H_{19}$ |
| 4e | GaCl | S | $C_{10}H_{21}$ |
| 4f | GaCl | O | $C_6H_{13}$ |
| 4g | GaCl | O | $C_7H_{15}$ |
| 4h | GaCl | O | $C_8H_{17}$ |
| 4i | GaCl | O | $C_9H_{19}$ |
| 4j | GaCl | O | $C_{10}H_{21}$ |
| 5a | InCl | S | $C_6H_{13}$ |
| 5b | InCl | S | $C_7H_{15}$ |
| 5c | InCl | S | $C_8H_{17}$ |

-continued

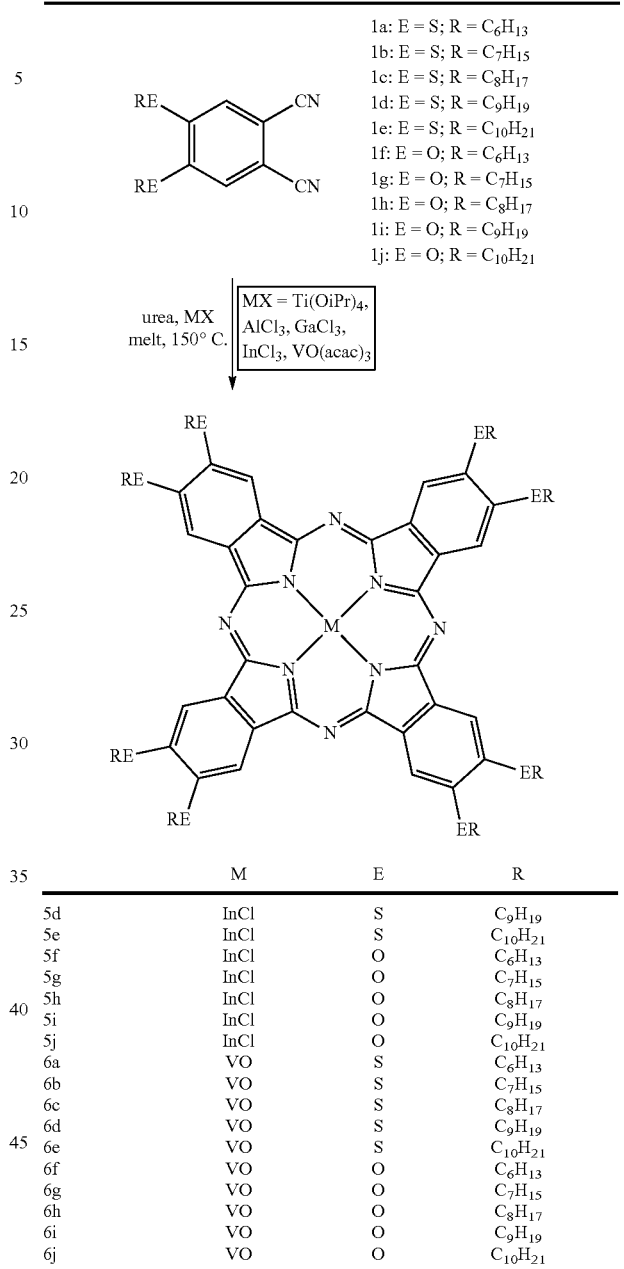

1a: E = S; R = $C_6H_{13}$
1b: E = S; R = $C_7H_{15}$
1c: E = S; R = $C_8H_{17}$
1d: E = S; R = $C_9H_{19}$
1e: E = S; R = $C_{10}H_{21}$
1f: E = O; R = $C_6H_{13}$
1g: E = O; R = $C_7H_{15}$
1h: E = O; R = $C_8H_{17}$
1i: E = O; R = $C_9H_{19}$
1j: E = O; R = $C_{10}H_{21}$ urea, MX melt, 150° C.
MX = Ti(OiPr)$_4$, AlCl$_3$, GaCl$_3$, InCl$_3$, VO(acac)$_3$

|    | M    | E | R           |
|----|------|---|-------------|
| 5d | InCl | S | $C_9H_{19}$ |
| 5e | InCl | S | $C_{10}H_{21}$ |
| 5f | InCl | O | $C_6H_{13}$ |
| 5g | InCl | O | $C_7H_{15}$ |
| 5h | InCl | O | $C_8H_{17}$ |
| 5i | InCl | O | $C_9H_{19}$ |
| 5j | InCl | O | $C_{10}H_{21}$ |
| 6a | VO   | S | $C_6H_{13}$ |
| 6b | VO   | S | $C_7H_{15}$ |
| 6c | VO   | S | $C_8H_{17}$ |
| 6d | VO   | S | $C_9H_{19}$ |
| 6e | VO   | S | $C_{10}H_{21}$ |
| 6f | VO   | O | $C_6H_{13}$ |
| 6g | VO   | O | $C_7H_{15}$ |
| 6h | VO   | O | $C_8H_{17}$ |
| 6i | VO   | O | $C_9H_{19}$ |
| 6j | VO   | O | $C_{10}H_{21}$ |

Phthalonitriles 1a-1e were synthesized by nucleophilic aromatic substitution of dichlorophthalonitrile with corresponding alkylthiols having different respective chain lengths. Macrocyclization of the substituted phthalonitrile was accomplished by heating molten phthalonitrile in the presence of titanium isopropoxide (Ti(iOPr)$_4$) and urea. The relative amount of non-metalated phthalocyanine (H$_2$Pc) formed as an undesirable side product was observed to depend on, inter alia, the presence of urea and on whether any solvent (1-pentanol in this instance) was present. Actually, the relative amount of H$_2$Pc was proportional to the amount of 1-pentanol. By eliminating 1-pentanol, the formation of H$_2$Pc can be completely eliminated. Consequently, the reaction became one that occurred in a melt (i.e., the reaction is "solvent-less").

The donor compounds resulting from the synthesis described above were purified by a combination of precipitation and flash chromatography. The compounds were characterized by mass spectrometry, UV-Vis spectroscopy, NMR, and elemental analysis. Matrix-Assisted Laser Desorption/Ionization (Time of Flight) ("MALDI-TOF") was used as a soft-ionization technique for mass spectrometry of the compounds. The base peak obtained with MALDI-TOF was a fixed mass unit greater than the molecular-ion peak for compounds 2a-2e. This suggested that the substituted TiOPc compounds underwent an in situ chemical reaction with the matrix. When MALDI-TOF was repeated with two different matrices [2-(4-hydroxyphenylazo)benzoic acid (HABA) and dithranol (DTH)], the base peaks were indeed found to correspond to respective products of in situ reactions between the alkylthio-substituted TiOPcs 2a-2e and the matrices. (Below, the alkylthio-substituted TiOPcs 2a-2e are termed "at-sTiOPcs.")

Figure 11A:
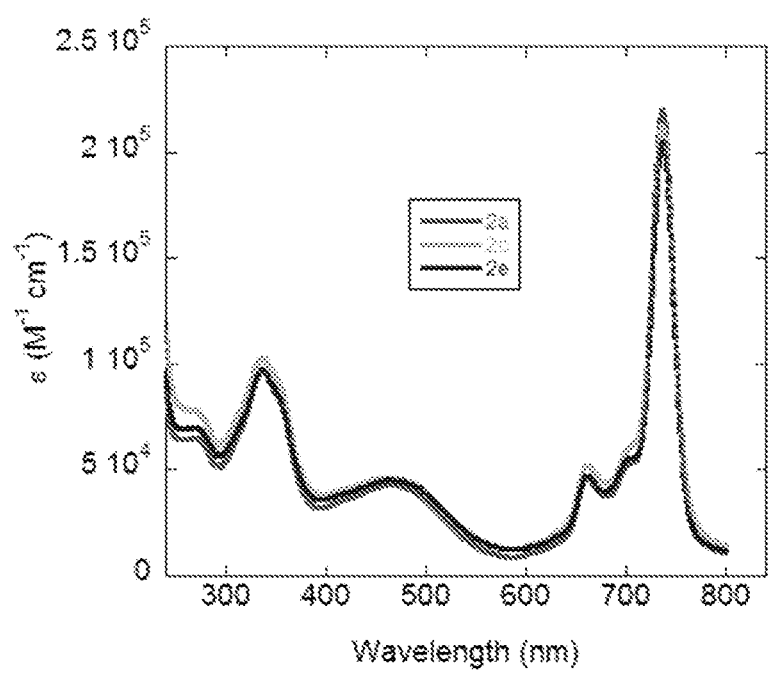
FIG. 11A includes plots of UV-Vis-NIR spectra of C6-, C8-, and C10-TiOPcs (compounds 2a, 2c, and 2e, respectively) as dissolved in solvent (DCM), as described in the second example.
Figure 11B:
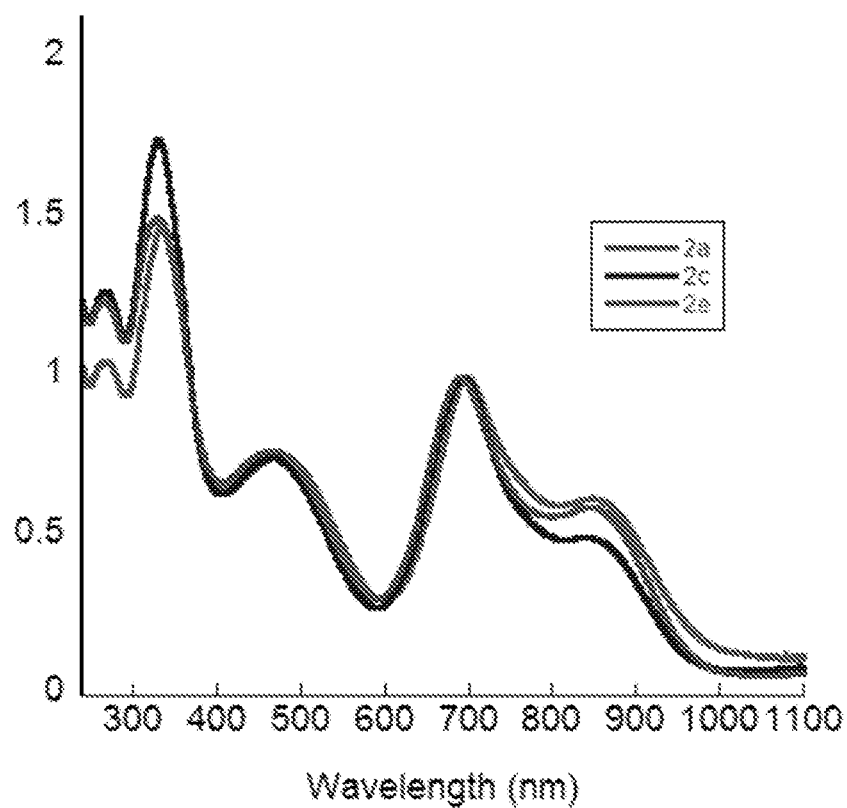
FIG. 11B includes plots of UV-Vis-NIR spectra of C6-, C8-, and C10-TiOPcs (compounds 2a, 2c, and 2e, respectively) in thin-film form (no solvent) as cast from DCM on a quartz substrate, as described in the second example.

Phthalocyanines 2a-2e exhibit intense Q and B absorption bands in the UV-visible spectrum (FIGS. 11A-11B). In dilute solutions, the Q and B absorption bands had $\lambda_{max}$ of approximately 736 and 366 nm, respectively. The Q band, which corresponds to the $\pi \to \pi^*$ electronic transition arising from a doubly degenerate HOMO to LUMO, is red-shifted about 36 nm relative to the unsubstituted TiOPc (FIG. 11A). This red-shift is typical of a phthalocyanine substituted with alkylthioethers at the β position that probably arises from the mixing of a 3p-orbital on sulfur with π-orbitals of the phthalocyanine core. The $Q_B$-band arises from electronic transitions from deeper level n-orbitals to the LUMO. The additional band around 400-500 nm, which is typical of TiOPc, is believed to be from charge-transfer from the electron-rich ring to the electron-poor metal.

The fate of an excited electron in a molecular crystal depends on the coupling of electric dipoles. Upon photoexcitation, an electron can either move from the HOMO to the LUMO within a molecule, leading to a Frenkel exciton. Alternatively, if there is strong dipole coupling, the electron can migrate to a neighboring molecule, producing a charge-transfer (CT) exciton. The degeneracy of ground and excited states is lifted due to molecular distortion ongoing from solution ($C_{4v}$) to condensed phase ($C_1$), which leads to a split Q-band in thin-film UV-Vis-NIR spectra (FIG. 11B). Apart from the absorption band around 700 nm, the new absorption band, which appears around 890 nm, is assigned to the CT excitonic band. The spin-forbidden CT band arises from the electronic transition from the ground state to the excited states, which are formed upon mixing of Frenkel and CT excitonic states. Hereinbelow, the bands around 700 and 890 nm are denoted as $Q_X$ and $Q_Y$, respectively.

This embodiment includes, formation of Phase-I-like and Phase-II-like polymorphs from soluble at-sTiOPcs by spin-coating respective solutions (in organic solvent) of the at-sTiOPcs. This embodiment also includes investigations of the effects of substituent chain lengths and casting solvents on the morphology of thin films of the at-sTiOPcs on quartz substrates, as used in OPV devices. The desired thin-film morphology was also obtained whenever the substrate was a PEDOT:PSS-coated ITO substrate (see first and second representative embodiments). The UV-Vis spectra for the at-sTiOPcs 2a, 2d, 2e were representative of the different polymorphs that were investigated.

Figure 12A:
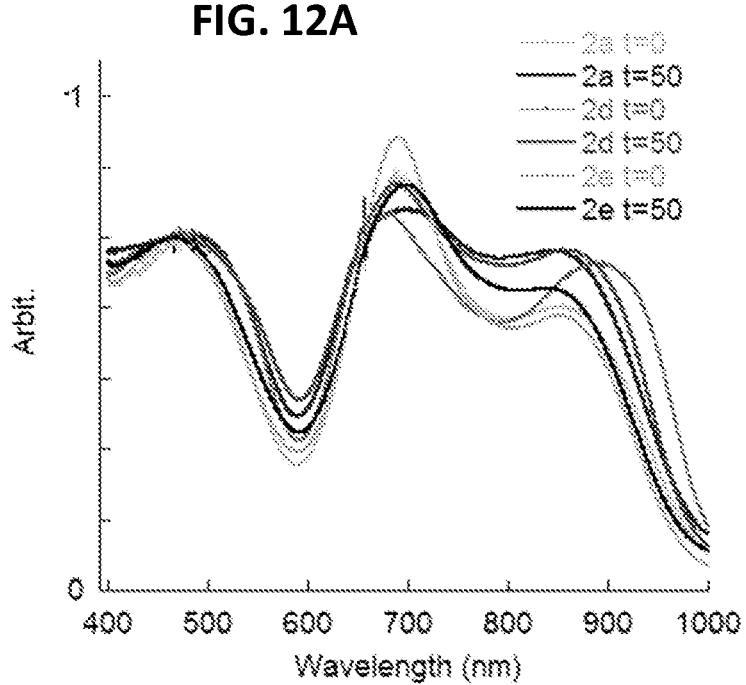
FIG. 12A includes plots of Vis-NIR spectra, particularly the Q bands, for TiOPcs 2a, 2d, and 2e, as cast from CHCl$_3$ onto quartz substrates, before annealing (t=0) and after annealing (t=50), as described in the second example.
Figure 12B:
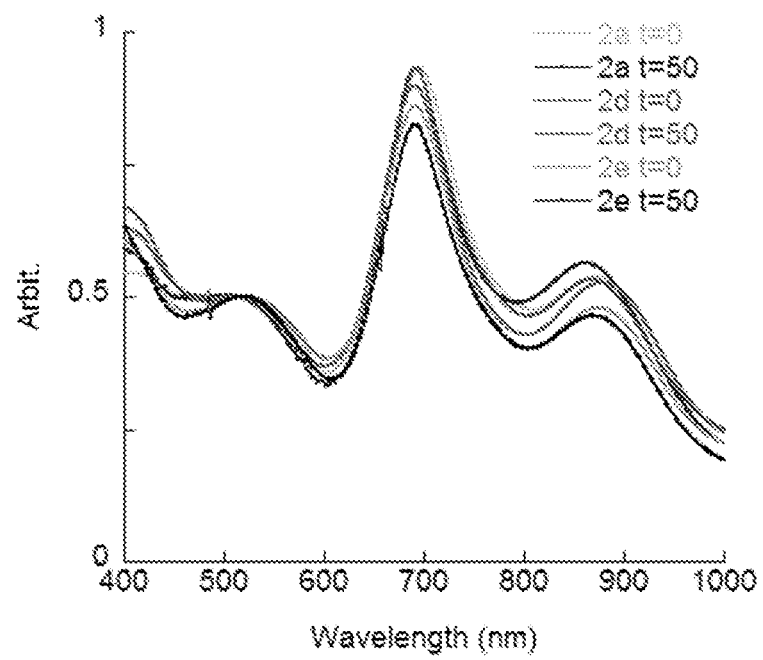
FIG. 12B includes plots of Vis-NIR spectra, particularly the Q bands, for TiOPcs 2a, 2d, and 2e, as cast from CHCl$_3$ onto PEDOT:PSS-coated ITO substrates, before annealing (t=0) and after annealing (t=50), as described in the second example.

Thin films of at-sTiOPcs were formed by drop-casting chloroform solutions thereof onto quartz or by spin-casting the same on PEDOT:PSS-coated ITO substrates. UV-Vis-NIR spectra of these films revealed $Q_X$ and $Q_Y$ bands, of which the $Q_X$ band was more intense, regardless of the substituent chain length (FIGS. 12A and 12B). However, the relative intensity of the $Q_Y$ band was greater when the films were cast on quartz compared to PEDOT:PSS-coated ITO substrate. This polymorph resembled phase-I, which arises from weak molecular distortions, and comprises a combination of $Q_X$ and $Q_Y$ excitonic bands, with the $Q_Y$ band appearing almost as a shoulder (FIG. 12A). Thermal annealing of the at-sTiOPc thin-films 2a-2e from $CHCl_3$ on a quartz substrate produced small increases in the $Q_Y$-band intensity, slight blue-shifting, and overall broadening of peaks (FIG. 12B).

Figure 13A:
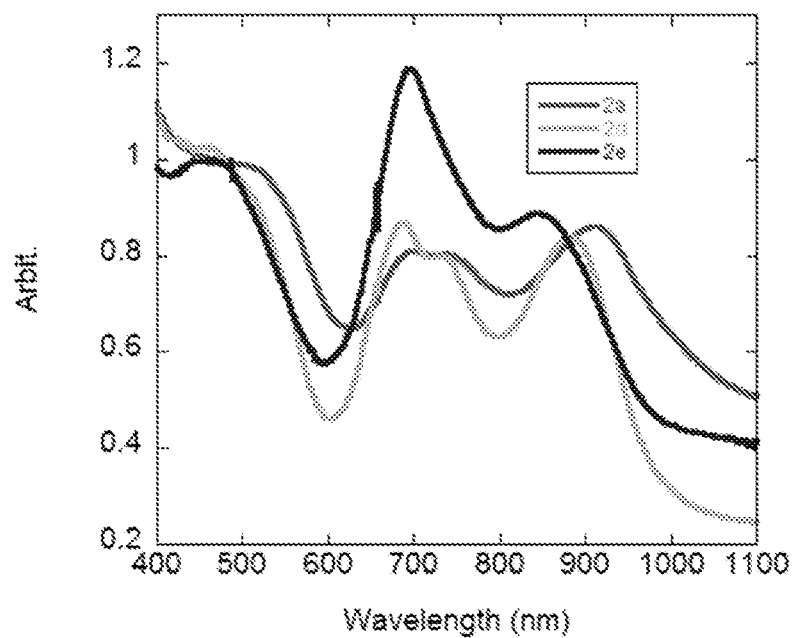
FIG. 13A includes plots of Vis-NIR spectra, particularly the Q bands, for TiOPcs 2a, 2d, and 2e for thin-films cast from ODCB on quartz substrates but with no annealing, as described in the second example.
Figure 13B:
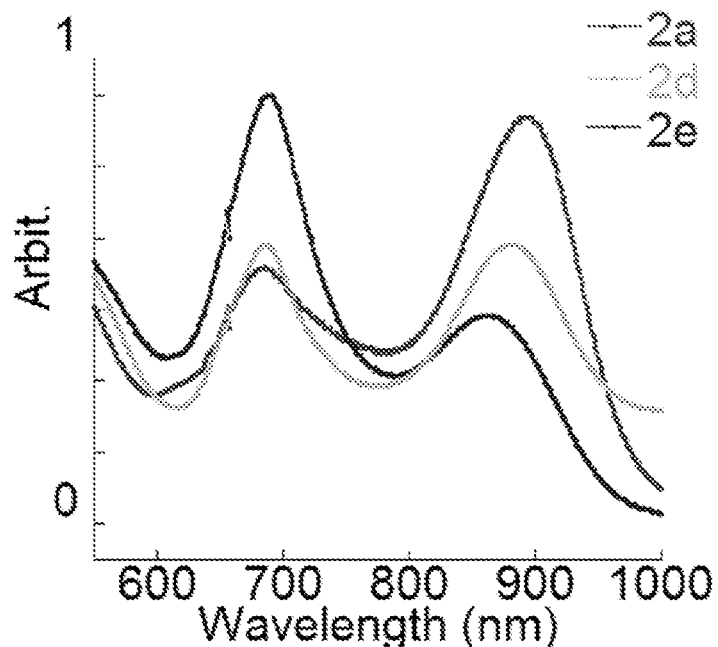
FIG. 13B includes plots of Vis-NIR spectra, particularly the Q bands, for TiOPcs 2a, 2d, and 2e for thin-films cast from ODCB on PEDOT:PSS-coated ITO but with no annealing, as described in the second example.
Figure 13C:
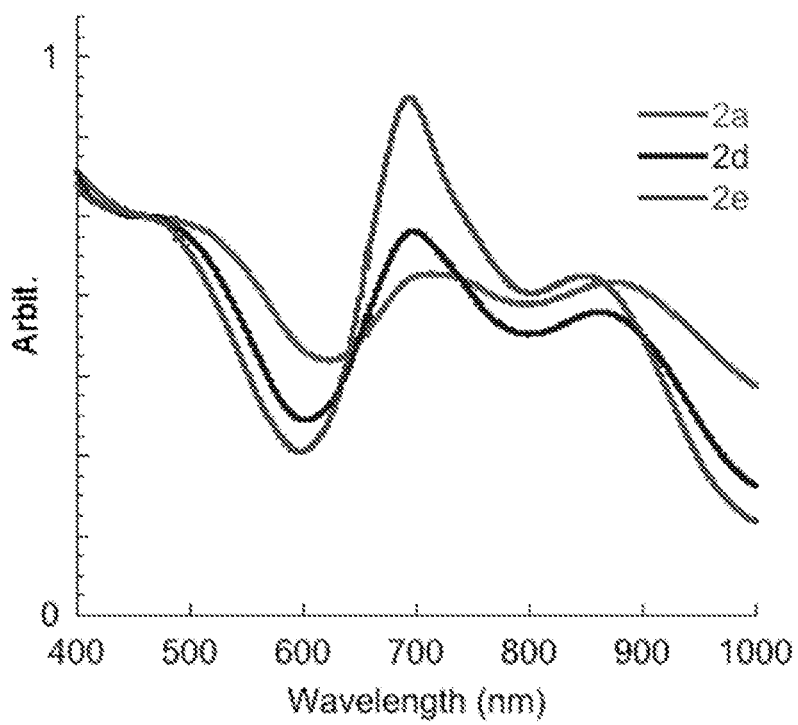
FIG. 13C includes plots of Vis-NIR spectra, particularly the Q bands, for TiOPcs 2a, 2d, and 2e for thin-films cast from ODCB on quartz substrates, with annealing, as described in the second example.
Figure 13D:
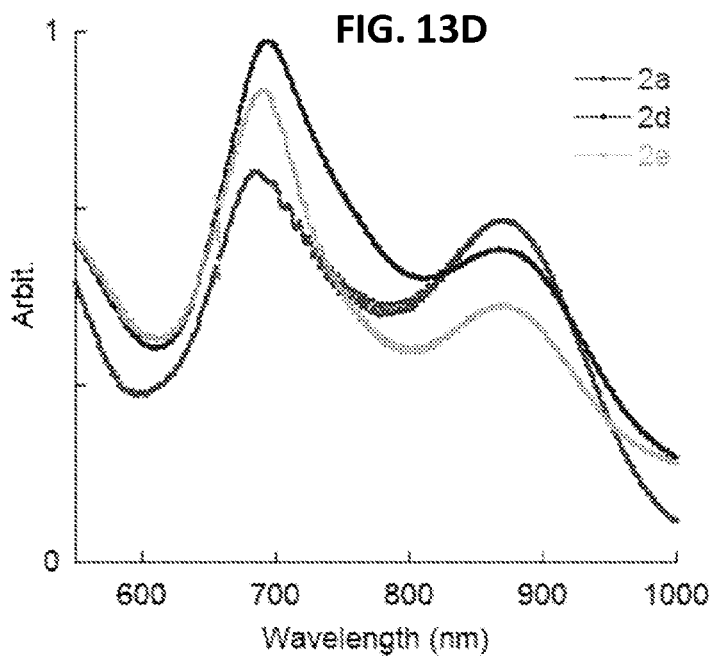
FIG. 13D includes plots of Vis-NIR spectra, particularly the Q bands, for TiOPcs 2a, 2d, and 2e for thin-films cast from ODCB on PEDOT:PSS-coated ITO, with annealing, as described in the second example.

When thin-films were spin-coated on quartz or PEDOT:PSS-coated ITO substrates from ortho-dichlorobenzene (ODCB), substituent-dependent polymorphisms were observed (FIGS. 13A-13D). The UV-Vis-NIR spectrum for at-sTiOPc 2a showed a more intense $Q_Y$ band relative to the $Q_X$ band. With at-sTiOPc 2d the relative intensities of $Q_X$ and $Q_Y$ bands are comparable, while for at-sTiOPc 2b, 2c, and 2e, the $Q_X$ band was more intense than the $Q_Y$ band. It is possible that the shorter-chain-length substituent on at-sTiOPc 2a allowed the molecules to become more packed, which may have led to substantial distortion. The longer-chain-length substituent in at-sTiOPcs 2b, 2c, and 2e may prevent close packing of molecules and hence, the extent of molecular distortion. At-sTiOPc 2d assumed a favorable molecular arrangement, in which the chain length seems to facilitate the organization in condensed phase, despite sterics. Thermal annealing of thin-films of at-sTiOPcs 2a-2e formed from ODCB on PEDOT:PSS-coated ITO substrates produced a decrease in $Q_Y$ band intensity, slight blue-shifting, and overall broadening of peaks (FIG. 13B). The blue-shift may be due, at least in part, to a partial formation of an H-type aggregate (Kasha's Rule), in which the molecules are co-facially aligned with each other.

Example 3

Figure 14A:
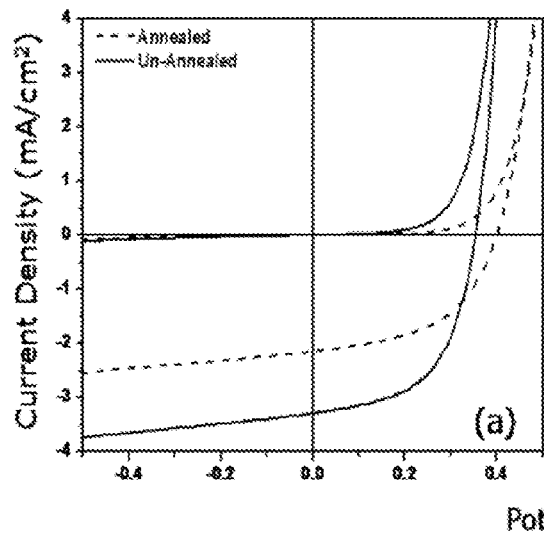
FIGS. 14A and 14B are respective linear and semilog plots of device performance for OPV devices based on C6-TiOPc/C$_{60}$, illuminated at 100 mW·cm$^{-2}$, as described in the second example.
Figure 14B:
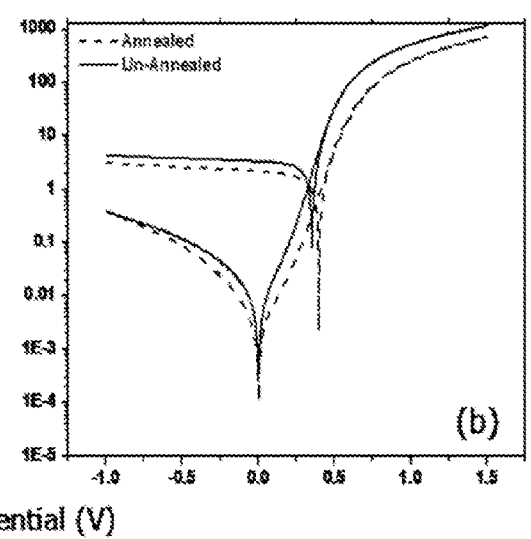

This example is directed to evaluations of the photovoltaic performances of the solution-processed alkylthio-substituted titanyl phthalocyanines ("at-sTiOPcs") described in the third representative embodiment. This example is particularly directed to the performance of at-sTiOPc 2a because of its enhanced absorption of near-IR wavelengths. PHJ devices were fabricated on ITO-coated (bottom contact) glass substrates modified with PEDOT:PSS as an electron-blocking layer. The at-sTiOPc thin-films were spin-coated from o-dichlorobenzene (ODCB), used as a solvent, and dried under ambient nitrogen pressure to form respective donor layers. The at-sTiOPc layer thickness was optimized by adjusting the speed and acceleration of spin-coating, and the concentration of the solution. Layer thickness was measured by AFM. Comparisons were made to thermally annealed, as-cast films. Subsequent vapor deposition of $C_{60}$ as the acceptor, bathocuprine (BCP) as the exciton-blocking layer, and aluminum (electrode) completed the devices. The non-annealed films exhibited higher short-circuit current densities ($J_{sc}$) compared to corresponding annealed films (FIGS. 14A-14B), which was consistent with the lower absorption coefficients for annealed films (FIG. 12B).

Figure 15A:
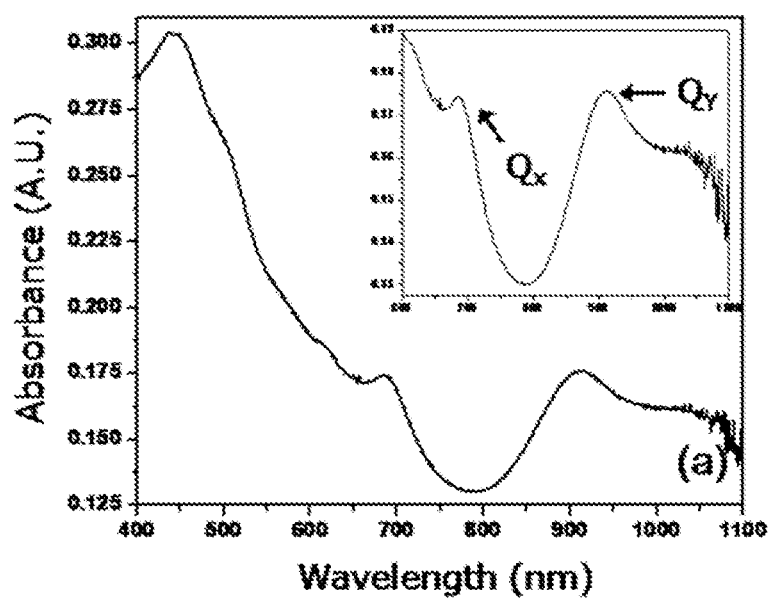
FIGS. 15A and 15B are respective plots of Vis-NIR spectra and IPCE for OPV devices having the device architecture: ITO/PEDOT:PSS/C6-TiOPc:C$_{60}$/BCP/Al, as described in the second example.
Figure 15B:
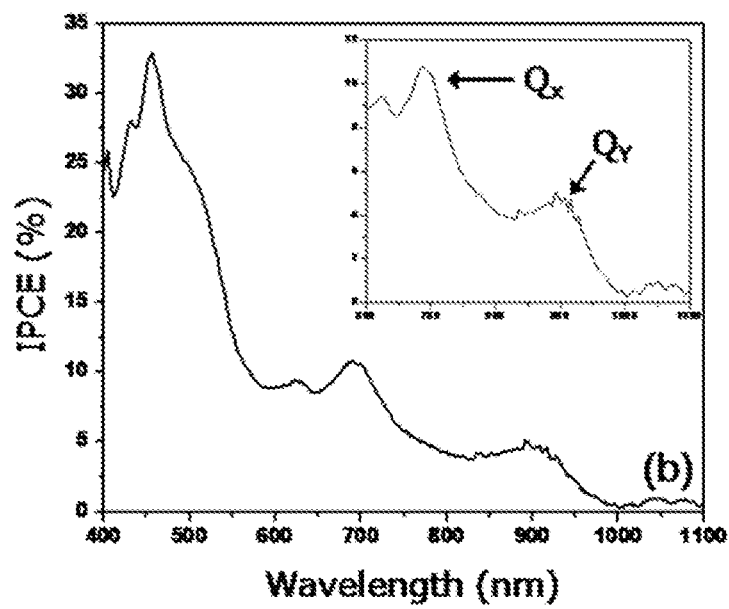

The annealed films exhibited higher open-circuit voltages ($V_{oc}$) compared to corresponding non-annealed films (Table 4). This behavior may be due to planarization of the at-sTiOPc 2a film occurring during thermal agitation; ultimately leading to less current because of a decrease in the interfacial surface area between the at-sTiOPc 2a layer and the acceptor layer, and an increase in photo-potential due to a reduction in pinholes, as evident from the lowering of the reverse saturation current (Table 4). The absorbance spectrum of the device was dominated by an absorption band at approximately 400-600 nm, comprising contributions from $C_{60}$ and at-sTiOPc 2a (FIG. 15A). The absorption bands at approximately 700 and 900 nm were contributed by the $Q_X$ and $Q_Y$ bands, respectively, of at-sTiOPc 2a. The contributions of these absorption bands to photocurrent were determined by an IPCE study. This study revealed that most of the photocurrent was from the 400-600 nm band (FIG. 15B). A lesser amount of photocurrent was contributed by the $Q_X$ band, which was consistent with the absorption spectrum (FIGS. 15A-15B). Despite strong absorption of the $Q_Y$ band in the near-IR, the contribution from this band to the overall current in the device was relatively low compared to from the $Q_X$ band.

Table 4, below, lists various device parameters for OPV devices constructed as PHJs of at-sTiOPc 2a and $C_{60}$.

TABLE 4

| Thickness (nm) | $V_{oc}$ (V) | $J_{sc}$ (mA/cm$^2$) | FF | $R_S$ | $R_P$ | $J_0$ | η |
|---|---|---|---|---|---|---|---|
| 3.5[a] | 0.39 | 3.17 | 0.40 | 0.810 | $1.04 \times 10^2$ | $3.54 \times 10^{-4}$ | 0.51% |
| 3.5[b] | 0.49 | 2.10 | 0.34 | 2.24 | $3.36 \times 10^3$ | $1.89 \times 10^{-4}$ | 0.35% |
| 5.5[a] | 0.35 | 3.29 | 0.55 | 0.80 | $1.96 \times 10^3$ | $3.36 \times 10^{-4}$ | 0.64% |
| 5.5[b] | 0.40 | 2.15 | 0.50 | 1.10 | $1.72 \times 10^3$ | $2.11 \times 10^{-4}$ | 0.43% |

[a]as-deposited films.
[b]annealed TiOPc/PEDOT:PSS/ITO film (150° C. for 10 min.
The parameters $V_{oc}$, $J_{sc}$, and FF are as discussed previously.
$R_s$ is series resistance, measured from far forward bias.
$R_p$ is shunt resistance, measured from far reverse bias.
$J_0$ is reverse saturation current, estimated from the lowest dark current (log plot).
η is power-conversion efficiency.

Experimental protocols for this example were as follows:

General Synthesis of Phthalonitriles 1a-1e

A mixture of alkane-1-thiol (2.5 equiv.), $K_2CO_3$ (5 equiv.) and DMSO was stirred at room temperature under argon for 30 min. Dichlorophthalonitrile (1 mmol) was added and the reaction mixture was maintained at 80° C. for 12 h. The reaction mixture was allowed to cool to room temperature, and then quenched with brine, extracted into ether, and washed with water. The solvent was removed under reduced pressure to obtain a yellow solid. Further purification was done with flash chromatography. Activated carbon was used to decolorize when necessary.

Synthesis of 4,5-bis(hexylthio)phthalonitrile 1a for Use in Making At-sTiOPc 2a

Following the general procedure, hexane-1-thiol (6.0 g, 50.74 mmol), $K_2CO_3$ (14.0 g, 101.29 mmol), dichlorophthalonitrile (4.0 g, 20.30 mmol) and DMSO (200 mL), after flash chromatography ($SiO_2$, 10:90 ethyl acetate/hexanes) produced the compound (5.17 g, 70%) as an off-white solid. Analytical data: mp=70-72° C.; $\delta^1$H NMR (500 MHz, CDCl$_3$) 7.38 (s, 2H), 3.00-2.97 (t, J=15 Hz, 4H), 1.75-1.69 (p, J=30 Hz, 4H), 1.50-1.44 (m, 4H), 1.32-1.29 (m, 8H), 0.90-0.87 (m, 6H); $^{13}$C NMR (125 MHz, CDCl$_3$) δ 144.2, 128.1, 115.6, 111.0, 32.7, 31.2, 28.5, 28.0, 22.4, 13.9; MS (EI) m/z 360.1 (M$^+$), $C_{20}H_{28}N_2S_2$ requires 360.1. Anal. calc'd for $C_{20}H_{28}N_2S_2$: C, 66.62; H, 7.83; N, 7.77. found: C, 66.74; H, 8.06; N, 8.02.

Synthesis of 4,5-bis(octylthio)phthalonitrile 1c for Use in Making At-sTiOPc 2c

Following the general procedure, octane-1-thiol (2.28 g, 15.60 mmol), $K_2CO_3$ (8.62 g, 62.40 mmol), dichlorophthalonitrile (1.23 g, 6.24 mmol) and DMSO (50 mL), after flash chromatography ($SiO_2$, 10:90 ethyl acetate/hexanes) produced the compound (2.23 g, 86%) as an off-white solid. Analytical data: mp=56-58° C.; $\delta^1$H NMR (500 MHz, CDCl$_3$) 7.42 (s, 2H), 3.04-3.01 (t, J=14.5 Hz, 4H), 1.79-1.73 (p, J=29.5 Hz, 4H), 1.53-1.47 (m, 4H), 1.33-1.29 (m, 16H), 0.91-0.88 (m, 6H); MS (EI) m/z 416.2 (M$^+$), $C_{24}H_{36}N_2S_2$ requires 416.2. Anal. calc'd for $C_{24}H_{36}N_2S_2$: C, 69.18; H, 8.71; N, 6.72. found: C, 69.17; H, 8.90; N, 6.57.

Synthesis of 4,5-bis(decylthio)phthalonitrile 1e for Use in Making At-sTiOPc 2e

Following the general procedure, decane-1-thiol (2.72 g, 15.60 mmol), $K_2CO_3$ (8.62 g, 62:40 mmol), dichlorophthalonitrile (1.23 g, 6.24 mmol) and DMSO (50 mL), after flash chromatography ($SiO_2$, 10:90 ethyl acetate/hexanes) produced the compound (2.25 g, 76%) as an off-white solid. Analytical data: $\delta^1$H NMR (500 MHz, CDCl$_3$) 7.38 (s, 2H), 3.00-2.97 (t, J=14.5 Hz, 4H), 1.75-1.69 (p, J=30 Hz, 4H), 1.47-1.43 (m, 4H), 1.33-1.25 (m, 24H), 0.87-0.84 (m, 6H): mp=54-56° C.; $^{13}$C NMR (125 MHz, CDCl$_3$) δ 144.6, 128.5, 116.0, 111.47, 33.2, 32.3, 29.9, 29.8, 29.7, 29.5, 29.3, 28.5, 23.1, 14.5; MS (EI) m/z 472.2 (M$^+$), $C_{28}H_{44}N_2S_2$ requires 472.2. Anal. calc'd for $C_{28}H_{44}N_2S_2$: C, 71.13; H, 9.38; N, 5.93. found: C, 70.81; H, 9.46; N, 6.10.

Synthesis of 2,3,9,10,16,17,23,24-octakis(hexylthio) phthalocyaninato-oxotitanium(IV) (2a)

A mixture of Pn 1a (4.1 g, 11.4 mmol) and urea (0.3 g, 5.7 mmol) was heated under argon to the melting point of the Pn (70° C.). Ti(iOPr)$_4$ (1.62 g, 5.70 mmol) was then added via syringe to the melt, and temperature was raised and maintained at 150° C. for 24 h. The reaction mixture was allowed to cool to room temperature, precipitated in methanol (100 mL), and centrifuged. The precipitate was dispersed and centrifuged in water (40 mL) and methanol (40 mL), sequentially. Finally, the brown-black precipitate was dispersed in acetone, filtered, and washed copiously with acetone until the filtrate was colorless. The precipitate was air-dried to obtain a black powder, which was then re-dissolved in a minimum amount of DCM and mixed with silica gel (30 g). Solvent was removed from the silica slurry on a rotary evaporator. The residuum was further dried under high vacuum to obtain a free-flowing powder, which was subjected to flash chromatography ($SiO_2$, 0:100 to 50:50 ethyl acetate/hexanes). After concentrating the eluted product, it was dispersed in acetone and then centrifuged. The precipitate was dried at 35-40° C. for 24 h under vacuum to obtain 2a (0.73 g, 16%) as a black solid: UV ($\lambda_{max}$, m) 736; $^1$H NMR δ (500 MHz, CDCl$_3$) 8.82-8.78 (br s, 8H), 3.56-3.45 (br s, 16H), 2.07 (br s, 16H), 1.75-1.68 (br s, 16H), 1.64-1.47 (br s, 32H), 0.98 (m, 24H); MS (MALDI) m/z 1505.7 [M+H]$^+$, C$_{80}$H$_{113}$N$_8$OS$_8$Ti requires 1505.6; 1714.9 [(MDTH)-OH]$^+$, C$_{94}$H$_{121}$N$_8$O$_3$S$_8$Ti requires 1714.7; 1730.0 [(MHABA)-OH]$^+$, C$_{93}$H$_{121}$N$_{10}$O$_3$S$_8$Ti requires 1730.6. Anal. calcd for C$_{80}$H$_{112}$N$_8$OS$_8$Ti: C, 63.79; H, 7.50; N, 7.44. Found: C, 63.42; H, 7.54; N, 7.50.

Synthesis of 2,3,9,10,16,17,23,24-octakis(heptylthio)phthalocyaninato-oxotitanium(IV) (2b)

Following procedure for 2a, Pn 1b (1.00 g, 2.57 mmol), urea (0.08 g, 1.3 mmol), and Ti(iOPr)$_4$ (0.37 g, 1.3 mmol), after flash chromatography afforded 2b (0.44 g, 42%) as a black solid: UV (λ$_{max}$, m) 736; $^1$H NMR δ (500 MHz, CDCl$_3$) 8.82-8.81 (br s, 8H), 3.61-3.35 (br s, 16H), 2.15 (br s, 16H), 1.71-1.70 (br s, 16H), 1.49-1.16 (br m, 48H), 0.92 (m, 24H); MS (MALDI) m/z 1618.8 [M+H]$^+$, C$_{88}$H$_{129}$N$_8$OS$_8$Ti requires 1618.7; 1826.7 [(MDTH)-OH]$^+$, C$_{102}$H$_{137}$N$_8$O$_3$S$_8$Ti requires 1826.8; 1841.9 [(MHABA)-OH]$^+$, C$_{101}$H$_{137}$N$_{10}$O$_3$S$_8$Ti requires 1841.8. Anal. calcd for C$_{88}$H$_{128}$N$_8$OS$_8$Ti: C, 65.31; H, 7.97; N, 6.92. Found: C, 64.86; H, 7.95; N, 7.02.

Synthesis of 2,3,9,10,16,17,23,24-octakis(octylthio)phthalocyaninato-oxotitanium(IV) (2c)

Following procedure for 2a, Pn 3 (0.88 g, 2.1 mmol), urea (0.06 g, 1.0 mmol), and Ti(iOPr)$_4$ (0.31 g, 1.1 mmol), after flash chromatography afforded 2c (0.31 g, 34%) as a black solid: UV nm) 736; $^1$H NMR δ (500 MHz, CDCl$_3$) 8.73-8.70 (br s, 8H), 3.47 (br s, 16H), 2.04 (br s, 16H), 1.93-1.90 (br s, 16H), 1.53-1.24 (br m, 64H), 0.90 (m, 24H); MS (MALDI) m/z 1730.8 [M+H]$^+$, C$_{96}$H$_{145}$N$_8$OS$_8$Ti requires 1730.8; 1938.9 [(MDTH)-OH]$^+$, C$_{110}$H$_{153}$N$_8$O$_3$S$_8$Ti requires 1938.9; 1953.1 [(MHABA)-OH]$^+$ C$_{109}$H$_{153}$N$_{10}$O$_3$S$_8$Ti requires 1953.9. Anal. calcd. for C$_{96}$H$_{145}$N$_8$OS$_8$Ti: C, 66.63; H, 8.39; N, 6.47. Found C, 66.23; H, 8.46; N, 6.61.

Synthesis of 2,3,9,10,16,17,23,24-octakis(nonylthio)phthalocyaninato-oxotitanium(IV) (2d)

Following procedure for 2a, Pn 1d (0.80 g, 1.50 mmol), urea (0.05 g, 0.8 mmol), and Ti($^i$OPr)$_4$ (0.37 g, 1.3 mmol), after flash chromatography afforded 2d (0.35 g, 42%) as a black solid: UV (λ$_{max}$, nm) 736; $^1$H NMR δ (500 MHz, CDCl$_3$) 8.73 (br s, 8H), 3.50 (br s, 16H), 2.06 (br s, 16H), 1.95 (br s, 16H), 1.75-1.24 (br m, 80H), 0.87-0.85 (m, 24H); MS (MALDI) m/z 1842.9 [M+H]$^+$, C$_{104}$H$_{161}$N$_8$OS$_8$Ti requires 1843.0; 2051.1 [(MDTH)-OH]$^+$, C$_{118}$H$_{169}$N$_8$O$_3$S$_8$Ti requires 2051.1; 2066.2 [(MHABA)-OH]$^+$, C$_{117}$H$_{169}$N$_{10}$O$_3$S$_8$Ti requires 2066.1. Anal. calcd. for C$_{104}$H$_{160}$N$_8$OS$_8$Ti: C, 67.78; H, 8.75; N, 6.08. Found C, 67.39; H, 8.84; N, 6.12.

Synthesis of 2,3,9,10,16,17,23,24-octakis(decylthio)phthalocyaninato-oxotitanium(IV) (2e)

Following procedure for 2a, Pn 1e (1.23 g, 2.60 mmol), urea (0.08 g, 1.3 mmol), and Ti($^i$OPr)$_4$ (0.37 g, 1.3 mmol), after flash chromatography afforded 2e (0.45 g, 35%) as a black solid: UV (λ$_{max}$, nm) 736.5; $^1$H NMR δ (500 MHz, CDCl$_3$) 8.73 (br s, 8H), 3.50 (br s, 16H), 2.06 (br s, 16H), 1.95 (br s, 16H), 1.75-1.24 (br m, 96H), 0.87-0.85 (m, 24H); MS (MALDI) m/z 1955.3 [M+H]$^+$, C$_{112}$H$_{177}$N$_8$OS$_8$Ti requires 1954.1; [(MDTH)-OH]$^+$ 2163.3, C$_{126}$H$_{185}$N$_8$O$_3$S$_8$Ti requires 2163.2; 2178.4 [(MHABA)-OH]$^+$, C$_{125}$H$_{185}$N$_{10}$O$_3$S$_8$Ti requires 2178.1. Anal. calcd. for C$_{112}$H$_{176}$N$_8$OS$_8$Ti: C, 68.81; H, 9.07; N, 5.73. Found C, 68.44; H, 8.93; N, 5.82.

Synthesis of 2,3,9,10,16,17,23,24-octakis(hexylthio)phthalocyaninato-chloroaluminum(III) (3a)

A mixture of 4,5-bis(hexylthio)phthalonitrile (1.0 g, 2.7 mmol), urea (83 mg, 1.4 mmol) and AlCl$_3$ (0.18 g, 1.4 mmol) was heated under argon at 150° C. for 36 h. The reaction mixture was allowed to cool to room temperature, dissolved in CH$_2$Cl$_2$ (4 mL), precipitated in methanol (160 mL), and centrifuged. The brown-black precipitate was air-dried, re-dissolved in CH$_2$Cl$_2$ (5 mL) and subjected to flash chromatography (SiO$_2$, 0:100 to 20:80 MeOH/CH$_2$Cl$_2$). After concentrating the eluted product, it was dispersed in MeOH and then centrifuged. The precipitate was dried at ca. 40° C. for 24 h under vacuum to obtain 3a (0.47 g, 45%) as a black solid: UV (λ$_{max}$, nm) 731; $^1$H NMR δ (500 MHz, CDCl$_3$) 8.37 (br s, 8H), 3.33 (br s, 16H), 2.12-0.97 (m, 64H); MS (MALDI) m/z [(MDTH)-HCl]$^+$ 1693.7, C$_{94}$H$_{121}$N$_8$O$_3$S$_8$Al requires 1693.7. Anal. calcd. for C$_{80}$H$_{112}$N$_8$S$_8$ClAl: C, 63.85; H, 7.50; N, 7.45. Found: C, 63.47; H, 7.15; N, 7.41.

Synthesis of 2,3,9,10,16,17,23,24-octakis(hexylthio)phthalocyaninato-chlorogallium(III) (4a)

Following the procedure for 3a, 4,5-bis(hexylthio)phthalonitrile (1.0 g, 2.8 mmol), urea (83 mg, 1.4 mmol) and GaCl$_3$ (0.25 g, 1.4 mmol), after flash chromatography (SiO$_2$, 0:100 to 10:80 MeOH/CH$_2$Cl$_2$), followed by precipitation in MeOH afforded 4a (0.33 g, 31%) as a black solid: UV (λ$_{max}$, nm) 733; $^1$H NMR (500 MHz, CDCl$_3$) δ 8.39 (m, 8H), 3.74-2.99 (m, 16H), 1.83 (m, 46H), 1.43 (br s, 18H), 1.18-0.95 (m, 24H); MS (MALDI) m/z [M+H]$^+$ 1547.5, C$_{80}$H$_{112}$N$_8$S$_8$ClGa requires 1546.5, [(MDTH)-HCl]$^+$ 1736.6, C$_{94}$H$_{121}$N$_8$O$_3$S$_8$Ga requires 1737.7. Anal. calcd. for C$_{80}$H$_{112}$N$_8$S$_8$ClGa: C, 62.09; H, 7.29; N, 7.24. Found: C, 62.44; H, 7.08; N, 7.23.

Synthesis of 2,3,9,10,16,17,23,24-octakis(hexylthio)phthalocyaninato-chloroindium(III) (5a)

Following the procedure for 3a, 4,5-bis(hexylthio)phthalonitrile (1.0 g, 2.7 mmol), urea (83 mg, 1.4 mmol) and InCl$_3$ (0.30 g, 1.4 mmol), after flash chromatography (SiO$_2$, 0:100 to 1:99 MeOH/CH$_2$Cl$_2$) followed by precipitation in MeOH, afforded 5a (0.50 g, 46%) as a black solid: UV (λ$_{max}$, nm) 734; $^1$H NMR δ (500 MHz, CDCl$_3$) 8.62 (br s, 8H), 3.57 (br s, 16H), 1.99 (br s, 16H), 1.65 (br s, 16H), 1.47 (br s, 32H), 1.01 (m, 24H); $^{13}$C NMR (125 MHz, CDCl$_3$) δ 151.3, 140.9; 133.9, 120.3, 33.9, 31.6, 29.0, 28.6, 22.6, 14.1; MS (MALDI) m/z 1593.8 [M+H]$^+$, C$_{80}$H$_{112}$N$_8$S$_8$ClIn requires 1593.5, [(MDTH)-HCl]$^+$ 1781.5, C$_{94}$H$_{121}$N$_8$O$_3$S$_8$In requires 7181.6. Anal. calcd. for C$_{80}$H$_{112}$N$_8$S$_8$ClIn: C, 60.33; H, 7.09; N, 7.04. Found: C, 60.71; H, 7.37; N, 7.35.

Synthesis of 2,3,9,10,16,17,23,24-octakis(hexylthio)phthalocyaninato-oxovanadium(IV) (6a)

Following the procedure for 3a, 4,5-bis(hexylthio)phthalonitrile (1.0 g, 2.8 mmol), urea (83 mg, 1.4 mmol) and VO(acac$_2$ (0.37 g, 1.4 mmol), after flash chromatography (SiO$_2$, 100% CH$_2$Cl$_2$), afforded 6a (0.33 g, 31%) as a black solid: UV ($\lambda_{max}$, nm) 737; $^1$H NMR (500 MHz, CDCl$_3$) δ 3.51 (br s, 16H), 2.04 (br s, 16H), 1.75 (br s, 16H), 1.47 (br s, 32H), 0.99 (br s, 24H); MS (MALDI) m/z [M+H]$^+$ 1507.5, $C_{80}H_{112}N_8OS_8V$ requires 1507.6. Anal. calcd. for $C_{80}H_{112}N_8OS_8V$: C, 63.66; H, 7.48; N, 7.42. Found: C, 63.40; H, 7.55; N, 7.45.

Substrate Preparation for High-Throughput Testing of OPV Devices:

ITO-coated glass (sheet resistance: ~15 Ω·cm$^2$) was pretreated by scrubbing with 10% Triton-X100 using a microfiber cloth, followed by successive sonications in 10% Triton-X100 (15 min), nanopure water (5 min), and absolute ethanol (15 min). The glass was then dried under a stream of nitrogen.

Substrate Preparation for Analytical Testing of OPV Devices:

The surface of ITO-coated glass (sheet resistance ~15 Ω·cm$^{-2}$) was flooded with positive photoresist (Rohm and Haas) and spun at 2000 RPM for 30 seconds. A shadow mask was used to pattern the ITO, followed by development of the ITO pattern. Aqua Regia (3:1) was pre-heated to 120° C., and the resist-coated ITO slides were immersed in same for 35 seconds. Removal of the photoresist followed. The ITO was then pretreated by scrubbing with 10% Triton-X100 using a micro-fiber cloth, followed by successive sonications in 10% Triton-X100 (15 min), nanopure water (5 min), and absolute ethanol (15 min). The substrates were then dried under a stream of nitrogen.

OPV Device Fabrication:

PEDOT:PSS was passed through a 0.45-micron filter before flooding ITO surfaces with respective 1 mL solutions thereof. The substrates were then spun at 3000 rpm (acceleration set to 225) for 1 min. The slides were transferred to a glove box and annealed therein at 175° C. (on a pre-equilibrated hot plate) followed by cooling to room temperature. The slides were allowed to dry at ambient nitrogen pressure. Annealing at-sTiOPc/PEDOT/ITO structures was performed at 150° C. for 10 min, as required. $C_{60}$ (MER Corp.) and bathocuproine (BCP, Sigma-Aldrich) were vacuum-deposited (approximately 1-2 Å·sec$^{-1}$) on top of at-sTiOPc 2a, sequentially, at a base pressure of approximately 10$^{-7}$ Torr using Knudsen-type sublimation cells. Vacuum-deposition was monitored using a 10$^-$ MHz quartz crystal microbalance (QCM-Newark) and an Agilent Technologies frequency monitor (Model 53131A). Aluminum was deposited (approximately 1-3 Å·sec$^{-1}$) at a base pressure of approximately 10$^{-6}$ Torr and monitored using a 6-MHz QCM (Tangidyne) and Inficon deposition monitor (model 758-500-G1). Respective regions in the center of these substrates were left open to allow absorbance spectra to be measured on the same films from which IPCE data were obtained.

OPV Device Testing:

Current density-voltage (J-V) data were obtained for a series of OPV device having a surface area of 0.019 cm$^2$. For obtaining IPCE data, devices having surface area of 0.125 cm$^2$ were used. The devices were tested inside a glove-box under ambient nitrogen pressure. Current density-voltage (J-V) measurements were made using a Keithley 2400 source meter. Data were acquired by in-house software created with Labview ver. 8.2 (National Instruments). The devices were scanned from −1.00 to +1.50 Volts with a 5-mV step size, starting from negative bias. A 250-W quartz-halogen lamp was used as an illumination source. The light was filtered through a 950-nm cutoff filter and through a sand-blasted light diffuser. The distance between the source and the device under test was adjusted to achieve an output of approximately 100 mW·cm$^{-2}$ per device, which was measured using a Newport thermopile photodetector (Model 818P-015-19).

IPCE measurements were obtained from devices placed in a sealed vessel containing a nitrogen atmosphere to prevent atmospheric oxidation of the devices. Light exposure was carried out using a 300-W xenon-arc lamp. Modulated light (250 Hz) from the source was passed through a monochromator, while spectra were acquired at 4-nm intervals. Incident power through the monochromator was measured with a calibrated Hamamatsu photodiode acquired from Newport Optics (Model 818-SL). Bias for the OPV device under test was maintained to obtain a short-circuit current at each wavelength. The current-to-voltage output was fed into an EG&G lock-in amplifier ((Model 5209), and output into in-house software created with Labview ver. 8.2 (National Instruments).

The third representative embodiment and this example demonstrate the development of an effective method for synthesis of a various alkylthioether-substituted TiOPc derivatives. The method eliminates the formation of non-metalated phthalocyanine, a side product that otherwise makes difficult the purification of the substituted TiOPcs. The at-sTiOPcs exhibit a substituent-dependent polymorphism in the condensed phase, when spin-cast or otherwise formed from o-dichlorobenzene on a quartz or PEDOT:PSS-coated ITO substrate. For example, at-sTiOPc 2a formed on quartz resembles phase-LI while at-sTiOPcs 2b, 2c, 2e resemble phase-I. At-sTiOPc 2d resembled an intermediate phase with comparable contributions from Frenkel and CT bands. The morphologies are retained when the films are formed on PEDOT:PSS-coated ITO substrates. An actual OPV device comprising at-sTiOPc 2a absorbed in the near-IR and exhibited good device characteristics.

Whereas the invention has been described in connection with representative embodiments, it will be understood that it is not limited to those embodiments. On the contrary, it is intended to encompass all alternatives, modifications, and equivalents as may be included within the spirit and scope of the invention as defined by the appended claims.

What is claimed is:

1. An organic photovoltaic device, comprising:
    a first electrode;
    a second electrode; and
    an organic, photovoltaically active zone located between the first and second electrodes, wherein the photovoltaically active zone comprises an organic electron-donor material, p-type, and an organic electron-acceptor material, the electron-donor and electron-acceptor materials forming at least one heterojunction, and
    the electron-donor material, p-type, comprises one or more trivalent- or tetravalent-metal phthalocyanines with alkylchalcogenide ring substituents at least one of which is thioalkyl substituent.

2. The organic photovoltaic device of claim 1, wherein the electron-donor material is soluble in at least one organic solvent.

3. The device of claim 1, wherein:
    the electron-donor material is configured as a first layer;
    the electron-acceptor material is configured as a second layer; and
    the heterojunction comprises a planar heterojunction defined at a planar interface between the first and second layers.

4. The device of claim 3, wherein the electron-donor material in the first layer of the planar heterojunction comprises at least one ($C_{5-12}$ alkyl)thio-substituted M-phthalocyanine (M-OPc), wherein M is a Ti=E, V=E, X—Al, X—Ga, or X—In, and wherein E is O, S, or Se, and X is Cl, Br, or I.

5. The device of claim 1, wherein the one or more trivalent- or tetravalent-metal phthalocyanines with alkyl-chalcogenide ring substituents comprises one or more compounds having the molecular formula:

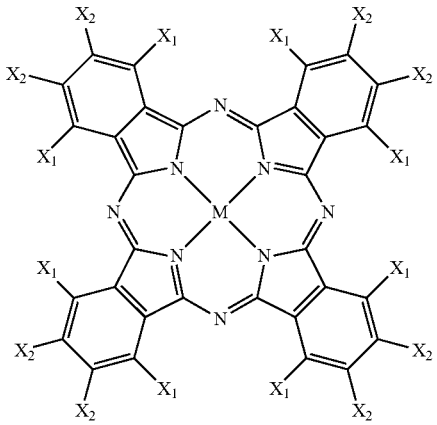

wherein M is a trivalent or tetravalent metal or metal group; $X_1$ is independently H, OR, or SR; $X_2$ is independently H, OR, or SR; OR is —O—R, where R is an alkyl or other hydrocarbon substituent containing 5-12 carbon atoms; SR is —S—R, where R is an alkyl or other hydrocarbon substituent containing 5-12 carbon atoms; and H is a hydrogen atom.

6. The device of claim 5, wherein M is a Ti=E, V=E, X—Al, X—Ga, or X—In, and wherein E is O, S, or Se, and X is Cl, Br, or I.

7. The device of claim 4, wherein the ($C_{5-12}$ alkyl)thio-substituted M-OPc comprises one or both of phase-1 and phase-2 polymorphs thereof.

8. The device of claim 3, wherein:
the first electrode is a transparent electrode;
the second electrode is a metal electrode; and
the device further comprises an exciton-blocking layer located between the first electrode and the first layer.

9. The device of claim 8, wherein:
the electron-donor material in the first layer of the photovoltaically active zone comprises at least one ($C_{5-12}$) thio-substituted M-phthalocyanine, wherein;
the electron-acceptor material comprises $C_{60}$ fullerene; and
the exciton-blocking layer comprises bathocuproin.

10. The device of claim 9, further comprising a layer of PEDOT:PSS between the first layer and the first electrode.

11. The device of claim 1, wherein the heterojunction comprises a bulk heterojunction of the electron-donor material and electron-acceptor material.

12. The device of claim 11, wherein the electron-donor material in the bulk heterojunction comprises at least one ($C_{5-12}$)thio-substituted titanium phthalocyanine (TiOPc).

13. The device of claim 12, wherein:
the first electrode is a transparent electrode;
the second electrode is a metal electrode; and
the device further comprises an exciton-blocking layer located between the first electrode and the bulk heterojunction.

14. The device of claim 13, further comprising a layer of PEDOT:PSS between the bulk heterojunction and the first electrode.

15. The device of claim 13, wherein:
the electron-donor material comprises at least one ($C_{5-12}$) thio-substituted titanium phthalocyanine (TiOPc);
the electron-acceptor material comprises PCBM; and
the exciton-blocking layer comprises LiF.

16. The device of claim 1, wherein the at least one trivalent- or tetravalent-metal phthalocyanine with alkyl-chalcogenide ring substituents absorbs and is photovoltaically sensitive to at least one visible light wavelength and at least one near-infrared wavelength.

17. The device of claim 1, wherein the at least one trivalent- or tetravalent-metal phthalocyanine with alkyl-chalcogenide ring substituents is a soluble ($C_{5-12}$)alkylthio-substituted titanium phthalocyanine (TiOPc).

18. The device of claim 17, wherein the alkylthio-substituted titanium phthalocyanine is an octa($C_{5-12}$ alkyl)thio-substituted TiOPc.

19. The device of claim 1, wherein:
the first electrode comprises ITO and is transparent to at least one wavelength to which the photovoltaically active zone is sensitive; and
the second electrode is a metal electrode and is reflective to the at least one wavelength.

20. The device of claim 1, further comprising a substrate supporting one of the first and second electrodes.

21. The device of claim 20, wherein the substrate is rigid or flexible and is transparent to at least one wavelength of electromagnetic radiation to which the photovoltaically active zone is sensitive.

22. An electronic device, comprising:
a load;
an organic photovoltaic device as recited in claim 1; and
a circuit connecting the organic photovoltaic device to the load.

23. An organic photovoltaic device, comprising:
a substrate transparent to at least one wavelength of visible light and at least one wavelength of near-IR light;
a cathode situated on the substrate, the cathode being transparent to the at least one wavelength of visible light and at least wavelength of near-IR light;
an anode; and
an organic, photovoltaically active zone sandwiched between the cathode and anode, the photovoltaically active zone comprising an organic electron-donor material, p-type, and an organic electron-acceptor material, the electron-donor and electron-acceptor materials forming at least one heterojunction, the electron-donor material comprising at least one soluble trivalent or tetravalent-metal phthalocyanine with alkylchalcogenide ring substituents at least one of which is thioalkyl substituent, the electron-donor material being absorptive and photovoltaically sensitive to the at least one visible wavelength and at least one near-IR wavelength.

24. The device of claim 23, wherein the heterojunction active zone comprises a planar heterojunction of the electron-donor material and the electron-acceptor material.

25. The device of claim 24, wherein the heterojunction comprise a bulk heterojunction of the electron-donor material and the electron-acceptor material.

26. The device of claim 23, wherein the at least one soluble trivalent or tetravalent-metal phthalocyanine with alkylchalcogenide ring substituents has the molecular formula:

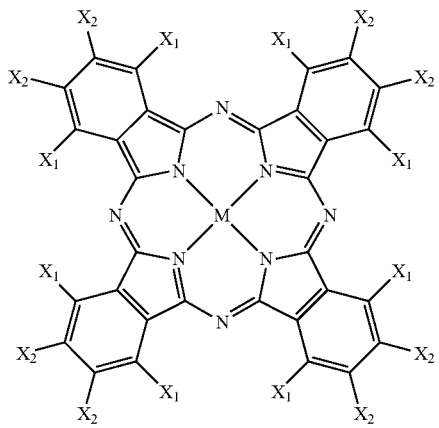

wherein M is a trivalent or tetravalent metal or metal group; $X_1$ is independently H, OR, or SR; $X_2$ is independently H, OR, or SR; OR is —O—R, where R is an alkyl or other hydrocarbon substituent containing 5-12 carbon atoms; SR is —S—R, where R is an alkyl or other hydrocarbon substituent containing 5-12 carbon atoms; and H is a hydrogen atom.

27. The device of claim 26, wherein M is a Ti=E, V=E, X—Al, X—Ga, or X—In, wherein E is O, S, or Se, and X is Cl, Br, or I.

28. An electronic device, comprising:
a load;
an organic photovoltaic device as recited in claim 23; and
a circuit connecting the organic photovoltaic device to the load.

29. A method for fabricating an organic photovoltaic device, comprising: solution-forming a photovoltaically active heterojunction of an electron donor material, p-type, and an electron accepting material, the electron-donor material comprising at least one trivalent- or tetravalent-metal phthalocyanine with one or more alkylchalcogenide ring substituents, each substituent group independently having five to twelve carbon atoms, and wherein at least one of which is thioalkyl substituent; and
situating the heterojunction between and in electrical contact with first and second electrodes.

30. The method of claim 29, further comprising annealing the heterojunction.

31. The method of claim 29, wherein forming the heterojunction comprises forming a planar heterojunction of the electron-donor and electron-accepting materials.

32. The method of claim 31, wherein forming the planar heterojunction comprises:
obtaining a liquid solution of the electron-donor material in an organic solvent;
forming the solution into an electron-donor layer in electrical contact with the first electrode;
applying a layer of the electron-accepting layer to the electron-donor layer, thereby forming a planar heterojunction; and
electrically coupling the second electrode to the electron-donor layer.

33. The method of claim 29, wherein forming the heterojunction comprises forming a bulk heterojunction of the electron-donor and electron-acceptor materials.

34. The method of claim 33, wherein forming the bulk heterojunction comprises:
preparing a solution comprising the electron-donor material in a solvent;
adding the electron-accepting layer to the solution to form a liquid mixture of the electron-donor and electron-accepting materials in the solvent;
forming the liquid mixture into a layer of which a first surface is in electrical contact with the first electrode; and
electrically coupling the second electrode to a second surface of the first electrode.

* * * * *